US012076183B2

(12) United States Patent
Shimizu et al.

(10) Patent No.: US 12,076,183 B2
(45) Date of Patent: Sep. 3, 2024

(54) IMAGE PROCESSING DEVICE AND IMAGE DISPLAY METHOD

(71) Applicants: TERUMO KABUSHIKI KAISHA, Tokyo (JP); Rokken Inc., Sakai (JP)

(72) Inventors: Katsuhiko Shimizu, Fujinomiya (JP); Yasukazu Sakamoto, Hiratsuka (JP); Ryosuke Saga, Osaka (JP)

(73) Assignees: TERUMO KABUSHIKI KAISHA, Tokyo (JP); ROKKEN INC., Sakai (JP)

( * ) Notice: Subject to any disclaimer, the term of this patent is extended or adjusted under 35 U.S.C. 154(b) by 0 days.

(21) Appl. No.: 17/043,055

(22) PCT Filed: Mar. 27, 2019

(86) PCT No.: PCT/JP2019/013473
§ 371 (c)(1),
(2) Date: Sep. 29, 2020

(87) PCT Pub. No.: WO2019/189518
PCT Pub. Date: Oct. 3, 2019

(65) Prior Publication Data
US 2021/0015452 A1 Jan. 21, 2021

(30) Foreign Application Priority Data
Mar. 29, 2018 (JP) ................................ 2018-066170

(51) Int. Cl.
*A61B 8/12* (2006.01)
*A61B 8/00* (2006.01)
*A61B 8/08* (2006.01)

(52) U.S. Cl.
CPC .............. *A61B 8/12* (2013.01); *A61B 8/0891* (2013.01); *A61B 8/463* (2013.01); *A61B 8/466* (2013.01); *A61B 8/5215* (2013.01)

(58) Field of Classification Search
None
See application file for complete search history.

(56) References Cited

U.S. PATENT DOCUMENTS 5,682,895 A 11/1997 Ishiguro
2002/0049375 A1 * 4/2002 Strommer ............ A61B 8/0833 600/407

(Continued)

FOREIGN PATENT DOCUMENTS

CN 101006933 A 8/2007
JP H0595949 A 4/1993

(Continued)

OTHER PUBLICATIONS

English Translation of WO 2016/140116; Shimizu et al.; 2016.*

(Continued)

*Primary Examiner* — Shahdeep Mohammed
(74) *Attorney, Agent, or Firm* — BUCHANAN INGERSOLL & ROONEY PC

(57) ABSTRACT

An image processing device includes a drive unit connected with an ultrasound element or an image sensor element, and an image processing unit that sequentially generates two-dimensional images of an organ, a blood vessel, or a medical instrument, based on information which is acquired by the ultrasound element or the image sensor element, and that generates a three-dimensional image based on the two-dimensional image. The image processing unit includes a storage unit that stores position correspondence information and/or image correspondence information, and a control unit that determines a position inside the three-dimensional image corresponding to a current position of the ultrasound element or the image sensor element, based on the position correspondence information or the image correspondence information, and that generates display information in real (Continued)

DRIVE UNIT
BASE
DISPLAY UNIT
INPUT UNIT
STORAGE UNIT
CONTROL UNIT
INFORMATION INPUT UNIT
ULTRASOUND ELEMENT
SHAFT
TUBE
ULTRASOUND TESTER time, in which the determined position inside the three-dimensional image is identified and displayed inside the three-dimensional image.

6 Claims, 18 Drawing Sheets

(56) References Cited

U.S. PATENT DOCUMENTS

| | | | | |
|---|---|---|---|---|
| 2005/0107688 | A1 | 5/2005 | Strommer | |
| 2006/0058647 | A1 | 3/2006 | Strommer et al. | |
| 2006/0241465 | A1 | 10/2006 | Huennekens et al. | |
| 2007/0167801 | A1 | 7/2007 | Webler et al. | |
| 2007/0238959 | A1 | 10/2007 | John et al. | |
| 2009/0088633 | A1 | 4/2009 | Meyer et al. | |
| 2009/0097778 | A1 | 4/2009 | Washburn et al. | |
| 2012/0022360 | A1 | 1/2012 | Kemp | |
| 2014/0200438 | A1* | 7/2014 | Millett | A61B 8/0841 600/463 |
| 2015/0022360 | A1* | 1/2015 | Chen | G06F 3/048 340/573.1 |
| 2015/0272472 | A1* | 10/2015 | Cathier | A61B 5/064 600/424 |
| 2016/0287278 | A1* | 10/2016 | Stigall | A61B 17/2202 |

FOREIGN PATENT DOCUMENTS

| | | | |
|---|---|---|---|
| JP | 2008512171 | A | 4/2008 |
| JP | 2008526387 | A | 7/2008 |
| JP | 2009090120 | A | 4/2009 |
| WO | 2016140116 | A1 | 9/2016 |

OTHER PUBLICATIONS

International Search Report (PCT/ISA/210) issued on Jun. 18, 2019, by the Japan Patent Office as the International Searching Authority for International Application No. PCT/JP2019/013473.

Written Opinion (PCT/ISA/237) issued on Jun. 18, 2019, by the Japan Patent Office as the International Searching Authority for International Application No. PCT/JP2019/013473.

An English-language version of the International Preliminary Report on Patentability (Form PCT/IB/373) and the Written Opinion of the International Searching Authority (Form PCT/ISA/237) issued on Sep. 29, 2020, by the International Bureau of WIPO in corresponding International Application No. PCT/JP2019/013473. (12 pages).

The extended European Search Report issued Mar. 24, 2021, by the European Patent Office in corresponding European Patent Application No. 19777555.4-1126. (8 pages).

Office Action (Communication pursuant to Article 94(3) EPC) issued Jun. 19, 2023, by the European Patent Office in corresponding European Patent Application No. 19 777 555.4-1126. (5 pages).

* cited by examiner

| POSITION ALONG Z-AXIS INSIDE THREE-DIMENSIONAL IMAGE | POSITION ALONG A-AXIS OF DRIVE UNIT |
| --- | --- |
| 1 | 1 |
| 2 | 2 |
| 3 | 3 |
| ⋮ | ⋮ |

FIG. 19

| POSITION ALONG Z-AXIS INSIDE THREE-DIMENSIONAL IMAGE | CROSS-SECTIONAL IMAGE ACQUIRED AND GENERATED BY ULTRASOUND ELEMENT AT EACH POSITION |
|---|---|
| 1 | CROSS-SECTIONAL IMAGE a |
| 2 | CROSS-SECTIONAL IMAGE b |
| 3 | CROSS-SECTIONAL IMAGE c |
| ⋮ | ⋮ |

IMAGE PROCESSING DEVICE AND IMAGE DISPLAY METHOD

TECHNICAL FIELD

The present disclosure relates to an image processing device and an image display method.

BACKGROUND ART

In the related art, a medical instrument is inserted into an organ such as a heart or a blood vessel (hereinafter, appropriately referred to as "organs") to perform a treatment on the organs. For example, PTL 1 discloses a technique for generating a three-dimensional image of the organs. A state of the organs can be recognized using the three-dimensional image of the organs which is generated in this way.

CITATION LIST

Patent Literature

[PTL 1] International Publication No. 2016/140116

SUMMARY OF INVENTION

Technical Problem

Incidentally, in order to perform a proper treatment on organs, it is important to recognize a time-dependent position of a medical instrument inside the organs. However, according to a peripheral information acquisition device such as an ultrasound transducer inserted into the organs, an observable area is limited, and it is difficult to display the time-dependent position of the medical instrument moving inside the organs.

In view of the above-described problem, an object of the present disclosure is to provide an image processing device and an image display method which are capable of displaying a time-dependent position of a medical instrument inside organs.

Solution to Problem

According to an aspect of the present invention, there is provided an image processing device including a drive unit connected with an ultrasound element or an image sensor element as a peripheral information acquisition device located inside a tubular member, and an image processing unit that sequentially generates two-dimensional images of an organ, a blood vessel, or a medical instrument, based on information on the organ, the blood vessel, or the medical instrument which is acquired by the ultrasound element or the image sensor element, and that generates a three-dimensional image of the organ, the blood vessel, or the medical instrument, based on the two-dimensional image. The drive unit moves the ultrasound element or the image sensor element along an extending direction of the tubular member. The image processing unit includes a storage unit that stores position correspondence information indicating a position along a predetermined coordinate axis inside the three-dimensional image which corresponds to a position of the drive unit and/or image correspondence information in which the position along the predetermined coordinate axis inside the three-dimensional image is associated with a plurality of the two-dimensional images, and a control unit that determines a position inside the three-dimensional image corresponding to a current position of the ultrasound element or the image sensor element, based on the position correspondence information or the image correspondence information, and that generates display information in real time, in which the determined position inside the three-dimensional image is identified and displayed inside the three-dimensional image.

In the image processing device according to an embodiment of the present invention, the storage unit may store the position correspondence information and correlation position correspondence information indicating a position of the ultrasound element or the image sensor element with respect to the position of the drive unit. The control unit may determine the position along the predetermined coordinate axis inside the three-dimensional image corresponding to the current position of the ultrasound element or the image sensor element, which is specified by a current position of the drive unit, based on the position correspondence information and the correlation position correspondence information.

In the image processing device according to an embodiment of the present invention, the drive unit may move at a constant speed. The control unit may sequentially generate current two-dimensional images showing an inner portion of the organ or the blood vessel at a predetermined time interval, based on the information acquired by the ultrasound element or the image sensor element at the current position, and may generate serial number information associated with the current two-dimensional image in an ascending order. The position correspondence information may include information on a moving speed of the drive unit and information on the predetermined time interval.

In the image processing device according to an embodiment of the present invention, the storage unit may store the image correspondence information. The control unit may generate a current two-dimensional image showing an inner portion of the organ or the blood vessel, based on the information acquired by the ultrasound element or the image sensor element at the current position, may extract a two-dimensional image similar to the current two-dimensional image from a plurality of the two-dimensional images included in the image correspondence information, and may determine the position along the predetermined coordinate axis inside the three-dimensional image corresponding to the extracted two-dimensional image, as the position inside the three-dimensional image corresponding to the current position of the ultrasound element or the image sensor element.

In the image processing device according to an embodiment of the present invention, the control unit may generate a current two-dimensional image showing an inner portion of the organ or the blood vessel, based on the information acquired by the ultrasound element or the image sensor element at the current position, and may add the two-dimensional image to the display information.

According to an aspect of the present invention, there is provided an image processing device including a drive unit connected with an ultrasound element or an image sensor element located inside a tubular member, and an image processing unit that sequentially generates two-dimensional images of an organ, a blood vessel, or a medical instrument, based on information on the organ, the blood vessel, or the medical instrument which is acquired by the ultrasound element or the image sensor element, and that generates a three-dimensional image of the organ, the blood vessel, or the medical instrument, based on the two-dimensional image. The drive unit causes the ultrasound element or the image sensor element to reciprocate along an extending direction of the tubular member. The image processing unit sequentially generates the two-dimensional images, based on the information acquired in a time-dependent manner while the ultrasound element or the image sensor element is caused to reciprocate by the drive unit.

In the image processing device according to an embodiment of the present invention, the image processing unit may include a storage unit that stores the two-dimensional image and the three-dimensional image.

In the image processing device according to an embodiment of the present invention, the image processing unit may specify the position of the ultrasound element or the image sensor element in the extending direction of the tubular member, based on the position of the drive unit in the extending direction of the tubular member.

In the image processing device according to an embodiment of the present invention, the drive unit may further rotate the ultrasound element or the image sensor element along a circumferential direction of the tubular member.

In the image processing device according to an embodiment of the present invention, the storage unit may further store information on a reciprocating range of the ultrasound element or the image sensor element. The drive unit may cause the ultrasound element or the image sensor element to reciprocate, based on the information on the reciprocating range.

In the image processing device according to an embodiment of the present invention, the image processing unit may further include an input unit capable of receiving an input of start point position information and end point position information. The storage unit may store the input start point position information and the input end point position information, as the information on the reciprocating range.

In the image processing device according to an embodiment of the present invention, the ultrasound element or the image sensor element may be capable of acquiring peripheral information on a periphery of the tubular member, along a plane orthogonal to the extending direction. The storage unit may further store position designation information for designating a predetermined position in the extending direction. The image processing unit may include a control unit that generates the two-dimensional image, based on the peripheral information acquired by the ultrasound element or the image sensor element at a position corresponding to the position designation information.

According to one aspect of the present invention, there is provided an image display method of an image processing device including a drive unit connected with an ultrasound element or an image sensor element located inside a tubular member, and an image processing unit that sequentially generates two-dimensional images of an organ, a blood vessel, or a medical instrument, based on information on the organ, the blood vessel, or the medical instrument which is acquired by the ultrasound element or the image sensor element, and that generates a three-dimensional image of the organ, the blood vessel, or the medical instrument, based on the two-dimensional image. The drive unit moves the ultrasound element or the image sensor element along an extending direction of the tubular member. The image processing unit includes a display unit capable of displaying the three-dimensional image, cross-sectional position information on the three-dimensional image, and the two-dimensional image at a position corresponding to the cross-sectional position information. The display unit simultaneously displays the three-dimensional image, the cross-sectional position information, and the two-dimensional image.

In the image display method according to an embodiment of the present invention, the display unit may display a plurality of the cross-sectional position information at different positions along a predetermined coordinate axis of the three-dimensional image, as the cross-sectional position information, and a plurality of the two-dimensional images corresponding to each of the plurality of cross-sectional position information, as the two-dimensional image.

In the image display method according to an embodiment of the present invention, the display unit may display a current position of the ultrasound element or the image sensor element, on the three-dimensional image.

Advantageous Effects of Invention

According to the image processing device and the image display method in the present disclosure, it is possible to display a time-dependent position of the medical instrument inside the three-dimensional image of the organs.

BRIEF DESCRIPTION OF DRAWINGS

FIG. 18 is a view illustrating an example of position correspondence information.

FIG. 19 is a view illustrating an example of image correspondence information.

DESCRIPTION OF EMBODIMENTS

Figure 1:
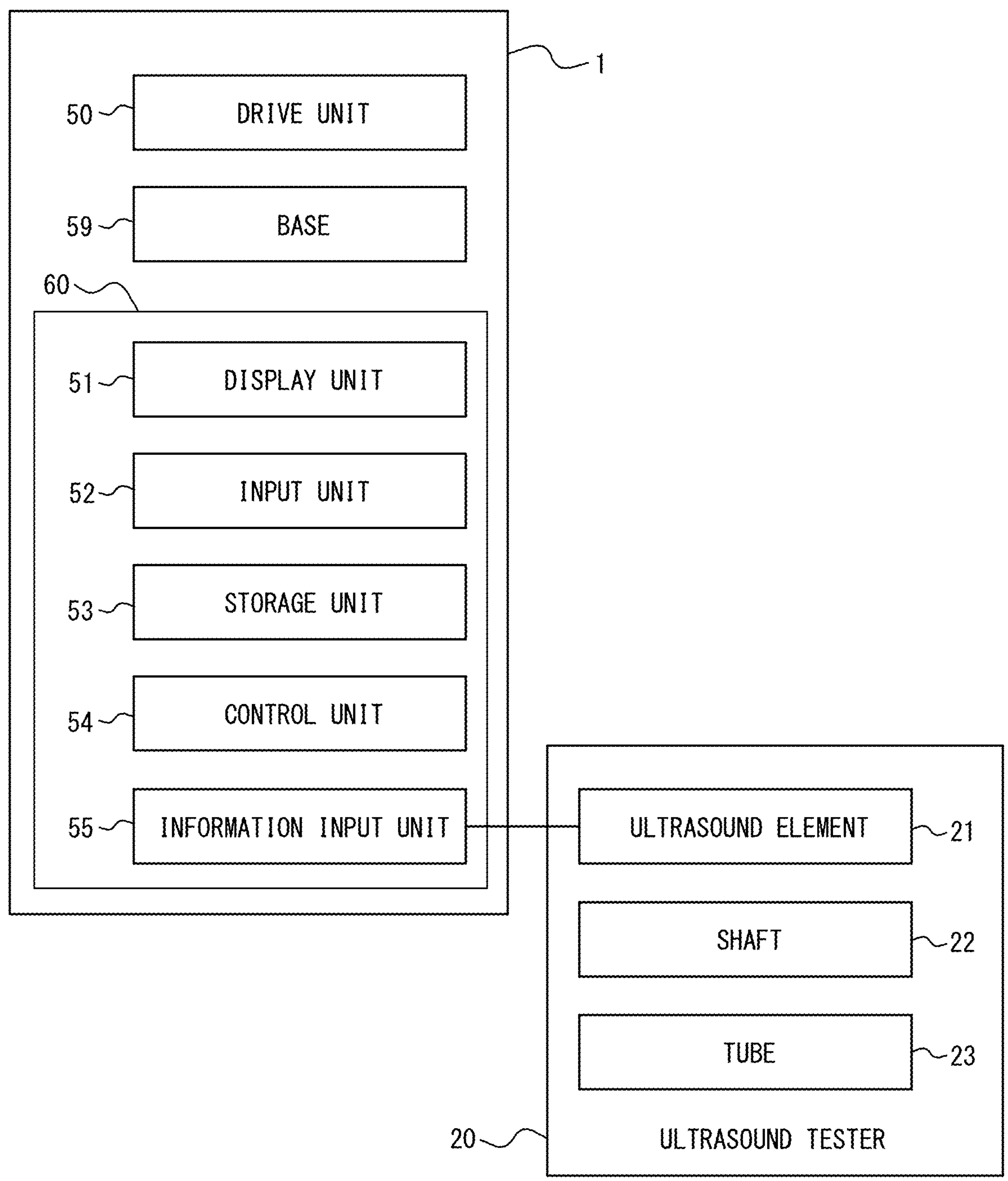
FIG. 1 is a block diagram illustrating a schematic configuration of an image processing device according to an embodiment of the present invention.

Hereinafter, an embodiment according to the present disclosure will be described with reference to the drawings. In each drawing, the same reference numerals will be assigned to common configuration elements. In addition, in the present specification, a side of a medical device 2 to be inserted into organs will be referred to as a "distally located side" or a "distal side", and an operating hand-side will be referred to as a "proximally located side" or a "proximal side".

[Image Processing Device 1]

Figure 2:
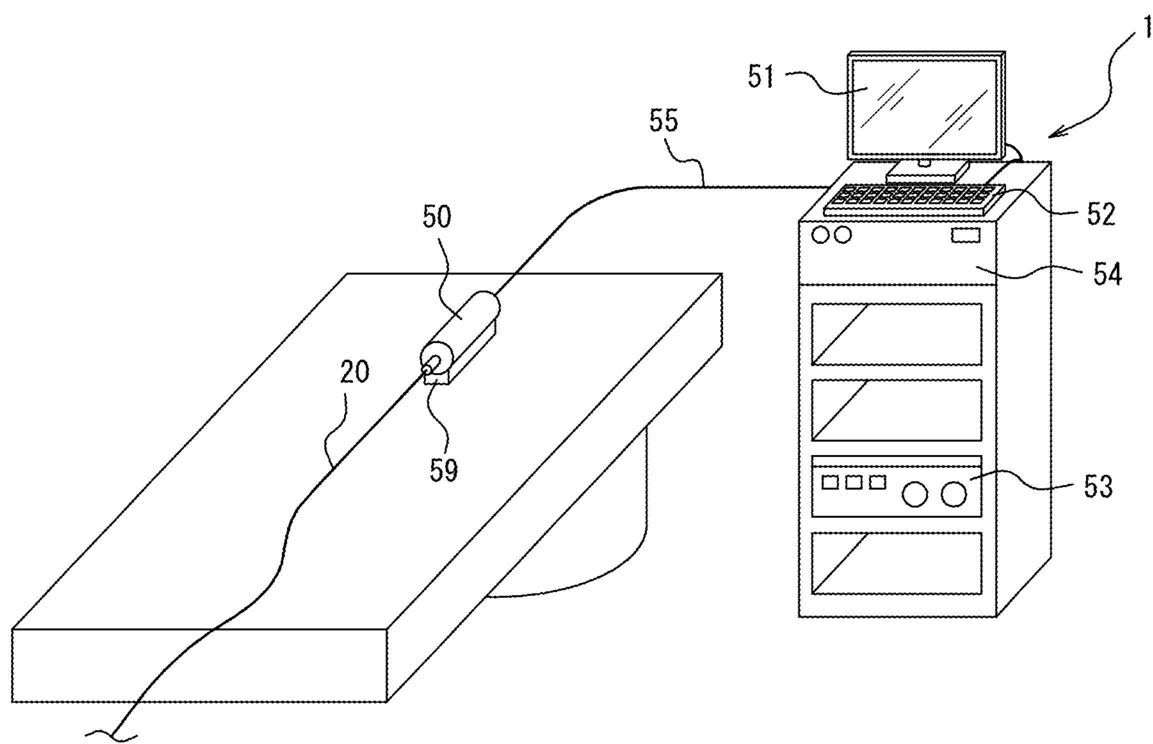
FIG. 2 is a schematic view of the image processing device illustrated in FIG. 1.

FIG. 1 is a block diagram illustrating a schematic configuration of an image processing device 1 according to an embodiment of the present disclosure. FIG. 2 is a schematic view of the image processing device 1. As illustrated in FIGS. 1 and 2, the image processing device 1 includes a drive unit 50, a base 59, and an image processing unit 60. The image processing unit 60 includes a display unit 51, an input unit 52, a storage unit 53, a control unit 54, and an information input unit 55. Although details will be described later, the image processing unit 60 generates a three-dimensional image, based on information on an organ, a blood vessel, or a medical instrument which is acquired by a peripheral information acquisition device such as an ultrasound element 21 (to be described later).

As illustrated in FIG. 1, the information input unit 55 is electrically connected to the ultrasound element 21 of an external ultrasound tester 20. The ultrasound tester 20 includes the ultrasound element 21, a shaft 22, and a tube 23.

The ultrasound element 21 as the peripheral information acquisition device acquires information on an organ such as a heart or a blood vessel (hereinafter, appropriately referred to as "organs"), or a medical instrument located inside the organs. Specifically, the ultrasound element 21 emits an ultrasound wave toward the organs or the medical instrument located inside the organs, and receives the ultrasound wave reflected from the organs or the medical instrument, as information. The image processing device 1 sequentially generates two-dimensional images of the organs or the medical instrument via the information input unit 55, based on the ultrasound wave as information received by the ultrasound element. Furthermore, the image processing device 1 generates and displays a three-dimensional image of the organs or the medical instrument, based on a plurality of the sequentially generated two-dimensional images.

As illustrated in FIG. 1, the drive unit 50 has a built-in motor, is connected with the ultrasound element 21 via the shaft 22, and causes the ultrasound element 21 to reciprocate along an extending direction of a catheter 40 (to be described later). Specifically, as illustrated in FIG. 2, the drive unit 50 fixes the ultrasound tester 20, and mounts the ultrasound tester 20 on the base 59. The drive unit 50 can reciprocate along the extending direction of the ultrasound tester 20 (that is, the extending direction of the catheter 40 to be described later) with respect to the base 59. Therefore, since the drive unit 50 itself reciprocates along the extending direction of the ultrasound tester 20, the drive unit 50 can cause the ultrasound element 21 to reciprocate along the extending direction of the catheter 40. Furthermore, the drive unit may rotate the ultrasound element 21 along a circumferential direction of the catheter 40 while causing the ultrasound element 21 to reciprocate. In this case, the drive unit 50 may continuously rotate the ultrasound element 21 in one direction, or may cause the ultrasound element 21 to oscillate while repeatedly changing a rotation direction.

The display unit 51 displays and outputs display information generated by the control unit 54. The display unit 51 includes a display device such as a liquid crystal display or an organic EL display, for example.

The input unit 52 receives an input of information or an instruction from an operator, and outputs received input information or received input instruction to the control unit 54. The input unit 52 includes an input device such as a keyboard, a mouse, or a touch panel, for example. In a case where the input unit 52 includes the touch panel, the touch panel may be disposed integrally with the display unit 51.

The storage unit 53 stores various information and programs for causing the control unit 54 to execute a specific function. In addition, the storage unit 53 stores the three-dimensional image of organs of a subject which is generated by the control unit 54. The storage unit 53 includes a storage device such as a RAM or a ROM, for example.

The control unit 54 controls an operation of each configuration element that configures the image processing device 1. The control unit 54 executes a specific function by reading a specific program. The control unit 54 includes a processor, for example.

The information input unit 55 receives an input of peripheral information on the organs or the medical instrument and the like located inside the organs which is acquired by the ultrasound element 21 as the peripheral information acquisition device. Specifically, the information input unit 55 is electrically connected to the ultrasound element 21 via a signal line extending inside the shaft 22, acquires a signal relating to peripheral information acquired by the ultrasound element 21, and transmits the signal to the control unit 54. The control unit 54 generates a two-dimensional image, based on the input information, and generates information on a position or an area of the organs or the medical instrument, based on the two-dimensional image.

For example, the ultrasound element 21 is located in a distal end of the ultrasound tester 20, and transmits and receives an ultrasound wave. The ultrasound element 21 can irradiate an object with the ultrasound wave, and can acquire information on a distance to the object and the like, based on the ultrasound wave reflected from the object. The shaft 22 is a flexible linear member which fixes the ultrasound element 21 in a distal portion and is connected with the drive unit 50 in a proximal portion. The tube 23 is a flexible tubular member that covers the shaft 22 in the circumferential direction. For example, the ultrasound element 21 is used by being inserted into the catheter 40 of the medical device 2 (to be described later). The ultrasound tester 20 and the medical device 2 (to be described later) may collectively configure one ultrasound catheter.

[Medical Device 2]

Figure 3:
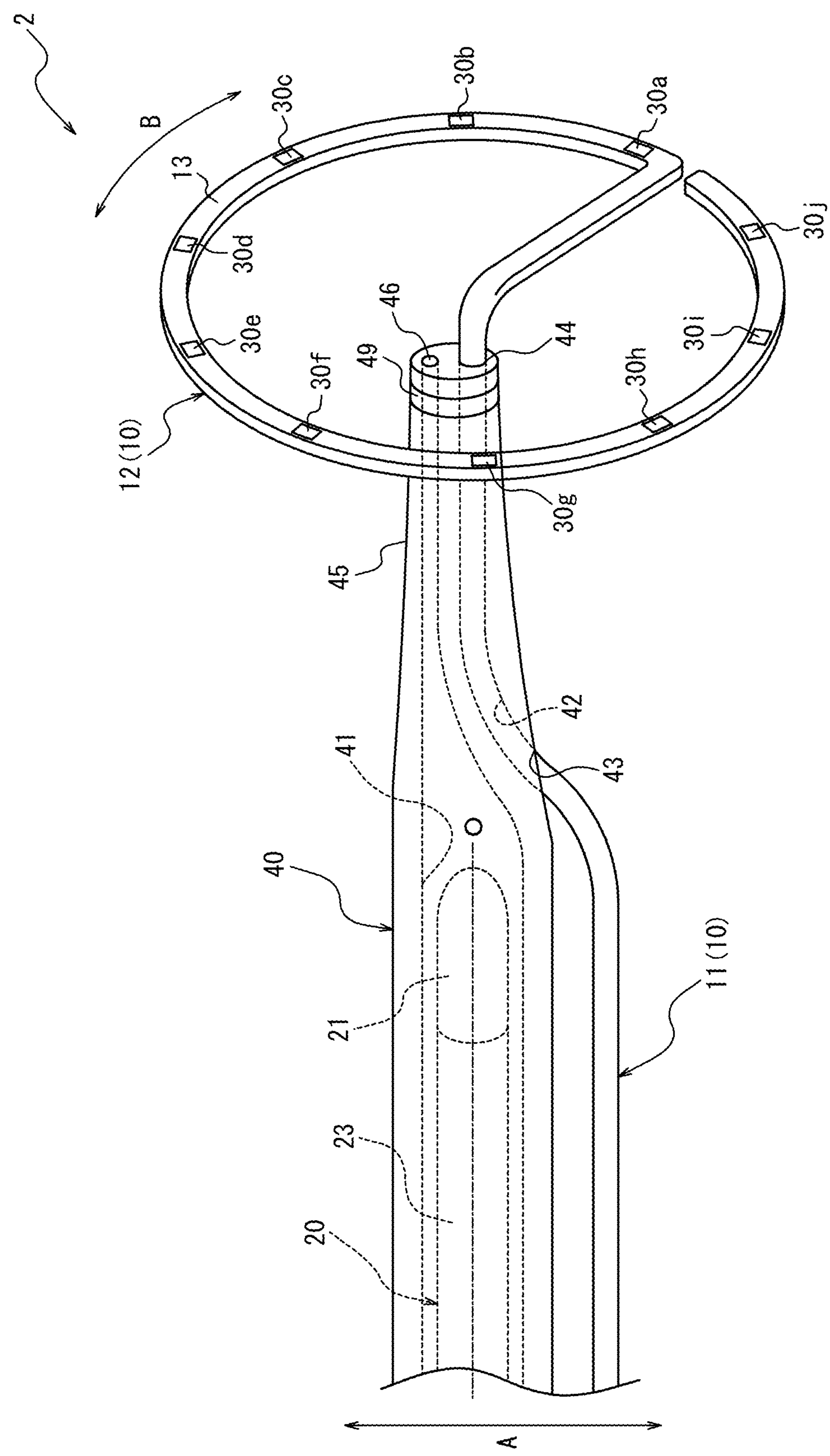
FIG. 3 is a perspective view of a medical device into which an ultrasound element is inserted.
Figure 4:
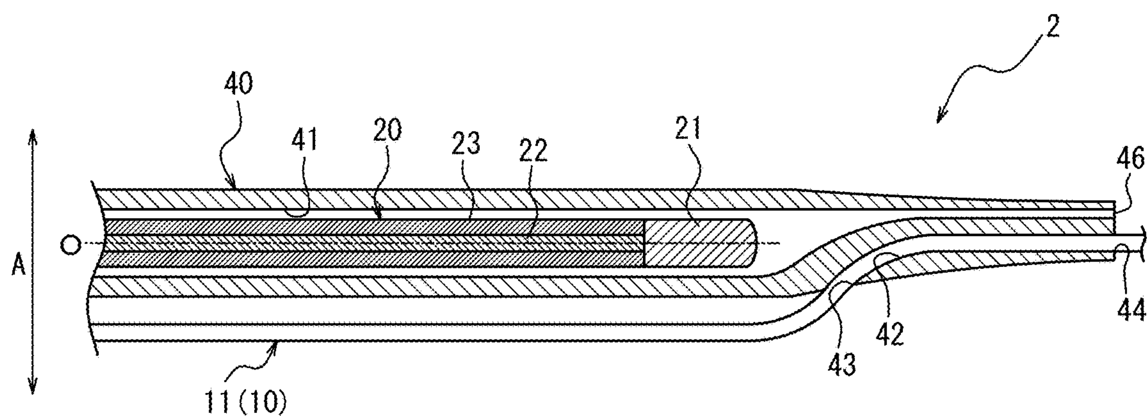
FIG. 4 is a sectional view of the medical device illustrated in FIG. 3.

FIG. 3 is a perspective view of the medical device 2 into which the ultrasound element 21 is inserted. FIG. 4 is a sectional view of the medical device 2, and FIG. 5 is a front view when the medical device 2 is viewed from the distally located side.

Figure 5:
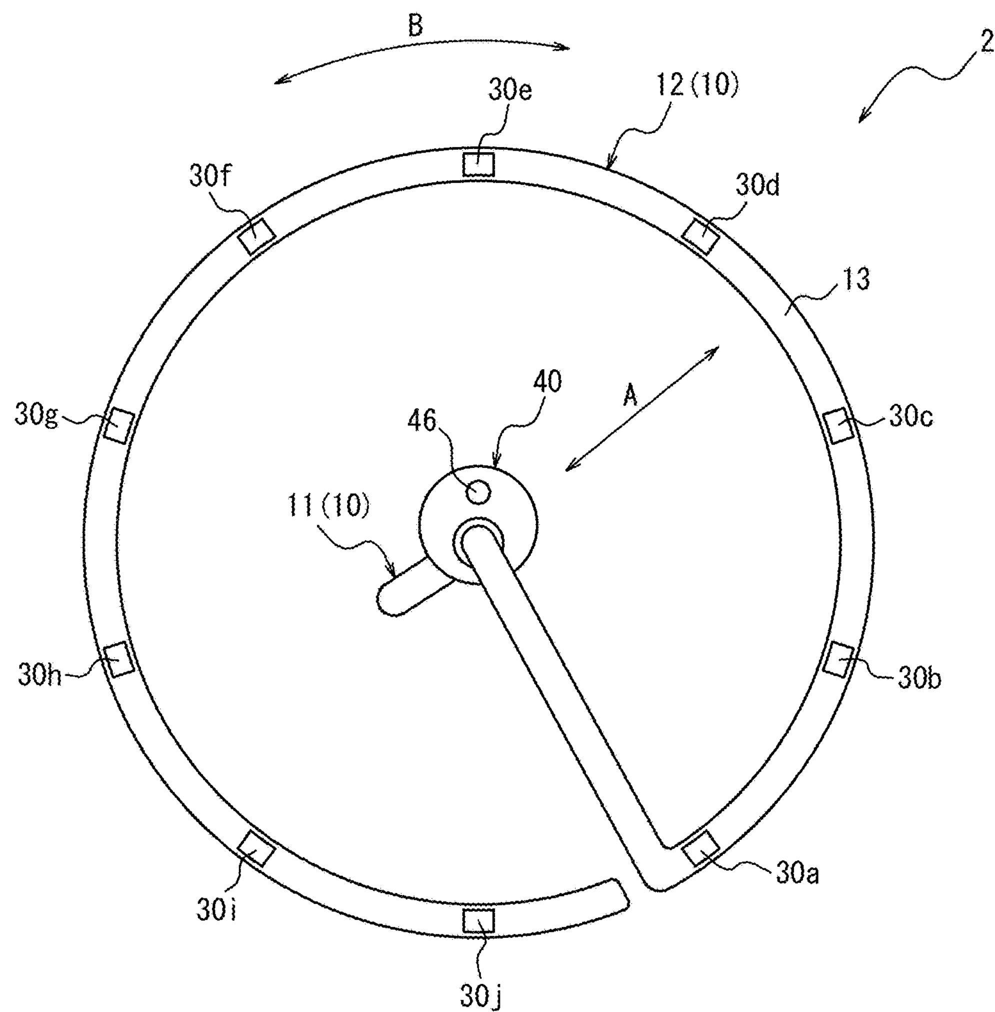
FIG. 5 is a front view when the medical device illustrated in FIG. 3 is viewed from a distally located side.

As illustrated in FIGS. 3 to 5, the medical device 2 includes a guide wire 10, electrodes 30*a* to 30*j*, and the catheter 40 as a tubular member. The catheter 40 internally defines a first lumen 41 into which the ultrasound tester 20 can be interpolated, and a second lumen 42 into which the guide wire 10 can be interpolated. FIGS. 3 to 5 illustrate a state where the ultrasound tester 20 is interpolated into the first lumen 41 and the guide wire 10 is interpolated into the second lumen 42. Hereinafter, unless otherwise specified, an example will be described in which the ultrasound tester 20 and the guide wire 10 are in states of being respectively interpolated into the first lumen 41 and the second lumen 42.

The guide wire 10 extends from the proximally located side to the distally located side. The guide wire 10 has a linear portion 11 and an annular expansive portion 12 disposed in an end portion on the distally located side connected with the linear portion 11. For example, the annular expansive portion 12 is made of metal such as a shape memory alloy, and is shape-memorized to annularly expand under an environment in which an external force acts in a prescribed or lower level.

In a state illustrated in FIGS. 3 and 5, the annular expansive portion 12 is located on the distally located side (distally located side communication hole 44 described later) from the distal end of the second lumen 42, and annularly expands. The annular expansive portion 12 expands outward in a radial direction A of the linear portion 11 of the guide wire 10, and extends along a circumferential direction B of the linear portion 11 of the guide wire 10. The annular expansive portion 12 has an outer diameter larger than that of the catheter 40 in an annularly expanded state. In addition, as illustrated in FIG. 3, in a case of being viewed from the distal side of the guide wire 10, the linear portion 11 of the guide wire 10 and the catheter 40 are located inside an annular shape of the annular expansive portion 12 that expands to have an annular shape larger than the outer diameter of the catheter 40. Hereinafter, even in a state where the annular expansive portion 12 annularly expands, the radial direction of the linear portion 11 of the guide wire 10 will be simply referred to as the "radial direction A", and the circumferential direction of the linear portion 11 of the guide wire 10 will be simply referred to as the "circumferential direction B". In addition, hereinafter, unless otherwise specified, description will be made on an assumption that the annular expansive portion 12 is in an annularly expanded state.

The electrodes 30*a* to 30*j* are fixed to the annular expansive portion 12, and are fixed at different positions in the extending direction of the annular expansive portion 12, that is, along the circumferential direction B of the guide wire 10. Hereinafter, in a case where the electrodes 30*a* to 30*j* are not distinguished from each other, all of these will be collectively referred to as a electrode 30.

When the electrode 30 is brought into contact with an inner wall of the organs, electrical characteristics of the inner wall of the organs can be detected. For example, as the electrical characteristics, it is possible to use a potential difference between the electrode 30 and another electrode that is in contact with another site of the organs. The electrode 30 is disposed to be exposed from a distal end 13 of the annular expansive portion 12, and the distal end 13 of the annular expansive portion 12 is pressed against the inner wall of the organs. In this manner, the electrode 30 can be brought into contact with the inner wall of the organs.

As illustrated in FIGS. 3 and 4, a central axis O of the ultrasound tester 20 extends along the extending direction of the catheter 40. The ultrasound element 21 rotates around the central axis O, and transmits and receives an ultrasound wave to acquire peripheral information on a plane orthogonal to the central axis O. Furthermore, the peripheral information acquired by the ultrasound element 21 is transmitted to the control unit 54 via the information input unit 55, and the control unit 54 generates a two-dimensional image of a plane orthogonal to the central axis O. Based on the obtained two-dimensional image, the control unit 54 can generate information on a position and an area of an inner wall surface of the organs, for example, such as information on the position and the area of the inner wall surface of the organs (hereinafter, referred to as "organ position information"). The control unit 54 can generate information on a position and an area of a medical instrument located outside the catheter 40 and inside the organs (hereinafter, referred to as "instrument position information"). Here, the ultrasound element 21 may obliquely transmit the ultrasound wave at a predetermined angle, for example, 3° to 18° in the radial direction. Since the ultrasound wave is obliquely transmitted at the predetermined angle in the radial direction, it is possible to suppress a possibility that the ultrasound wave reflected from an inner peripheral surface of the first lumen 41 may be detected (ring down).

The ultrasound element 21 receives the ultrasound wave reflected from the linear portion 11 of the guide wire 10. In this manner, the ultrasound element 21 can acquire ultrasound information corresponding to the instrument of the guide wire 10 in the circumferential direction around the central axis O. The peripheral information acquired by the ultrasound element 21 is transmitted to the control unit via the information input unit 55. After the two-dimensional image is generated based on the input peripheral information, the control unit 54 can estimate the position and the area of the guide wire 10, based on the two-dimensional image.

As illustrated in FIG. 4, the shaft 22 fixes the ultrasound element 21 in the distal end along the central axis O. The shaft 22 is rotatable around the central axis O along the circumferential direction of the catheter 40. The ultrasound element 21 rotates around the central axis O in conjunction with the rotation of the shaft 22. In this manner, the ultrasound element 21 can acquire the peripheral information around the central axis O. In addition, the shaft 22 is movable along the central axis O, that is, along the extending direction of the catheter 40. The ultrasound element 21 moves along the central axis O in conjunction with the movement of the shaft 22 along the central axis O. In this manner, the ultrasound element 21 can acquire the peripheral information along the central axis O. The peripheral information acquired here is sequentially transmitted to the control unit 54. The control unit 54 generates a two-dimensional image of a plane orthogonal to the central axis O. When the shaft 22 moves along the central axis O, the tube 23 also moves in conjunction with the movement of the shaft 22. The outer diameter of the shaft 22 is smaller than the outer diameter of the ultrasound element 21.

As illustrated in FIG. 4, the tube 23 is a flexible tubular member that covers the shaft 22 in the circumferential direction. Since the tube 23 is in close contact with the shaft 22, the tube 23 can slide in the extending direction with respect to the catheter 40 without hindering the rotation and movement of the shaft 22. In addition, the proximal portion of the tube 23 is harder than the distal portion of the tube 23 so that a hand-side pushing force on the proximal side of the ultrasound tester 20 is easily transmitted to the distal side of the ultrasound tester 20.

As illustrated in FIGS. 3 and 4, the catheter 40 is a rapid exchange (RX) type catheter which has a distal portion 45 that is an end portion on the distally located side and a proximal portion (not illustrated) that is an end portion on the proximally located side, and in which the second lumen 42 is partitioned only in the distal portion 45. The first lumen 41 of the catheter 40 communicates with a portion from the distal portion 45 of the catheter 40 to the proximal portion (not illustrated). In other words, the first lumen 41 communicates with the outside through an opening (not illustrated) disposed in the proximal portion, and communicates with the outside through an opening 46 disposed in the distal portion 45 so that priming can be performed. It is preferable that the inner diameter of the opening 46 is smaller than the outer diameter of the ultrasound element 21. This configuration suppresses a possibility that the ultrasound element 21 interpolated in the first lumen 41 may be discharged outward through the opening 46. Accordingly, the position of the ultrasound element 21 is restricted to be located on the proximal side from the annular expansive portion 12 of the guide wire 10. The ultrasound element 21 is movable with respect to the guide wire 10 in the extending direction of the guide wire 10. In addition, the first lumen 41 is partitioned on an inner side of the guide wire 10 in the radial direction A from the annular expansive portion 12 of the guide wire 10. Accordingly, the ultrasound element 21 is disposed on the inner side of the guide wire 10 in the radial direction A from the annular expansive portion 12. The catheter 40 is not limited to the RX type catheter, and may be a catheter having other shapes, for example, an over-the-wire (OTW) type catheter. However, as described above, it is preferable to use the RX type catheter in view of an easy configuration.

As illustrated in FIG. 4, the second lumen 42 of the catheter 40 is located in the distal portion 45 in a direction orthogonal to the extending direction of the first lumen 41. The second lumen 42 extends along the extending direction of the first lumen 41. In this example, the second lumen 42 extends from a proximally located side communication hole 43 formed on a side surface of the catheter 40 to a distally located side communication hole 44 formed in the distal end of the catheter 40. The first lumen 41 and the second lumen 42 have the above-described positional relationship. Accordingly, the ultrasound element 21 can be disposed along the extending direction of the linear portion 11 on the proximal side from the annular expansive portion 12 of the guide wire 10. In addition, the guide wire 10 is interpolated in a state of penetrating the second lumen 42, and can freely move in the extending direction with respect to the catheter 40. In this case, the linear portion 11 of the guide wire 10 is located in the direction orthogonal to the axial direction of the ultrasound element 21. The inner diameter of the second lumen 42 is smaller than the inner diameter of the first lumen 41.

[Organ Information Acquisition Method]

Figure 6:
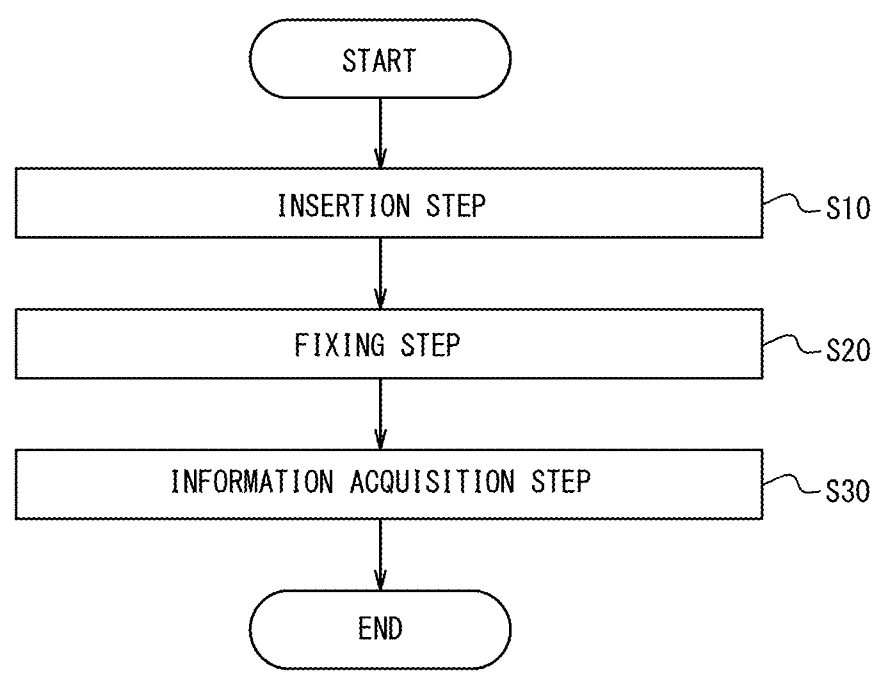
FIG. 6 is a flowchart illustrating an organ information acquisition method using the ultrasound element.

FIG. 6 is a flowchart illustrating an organ information acquisition method using the ultrasound element 21 located in the first lumen 41 inside the catheter 40. As illustrated in FIG. 6, the organ information acquisition method sequentially includes an insertion step (Step S10), a fixing step (Step S20), and an information acquisition step (Step S30) in time series.

Figure 7:
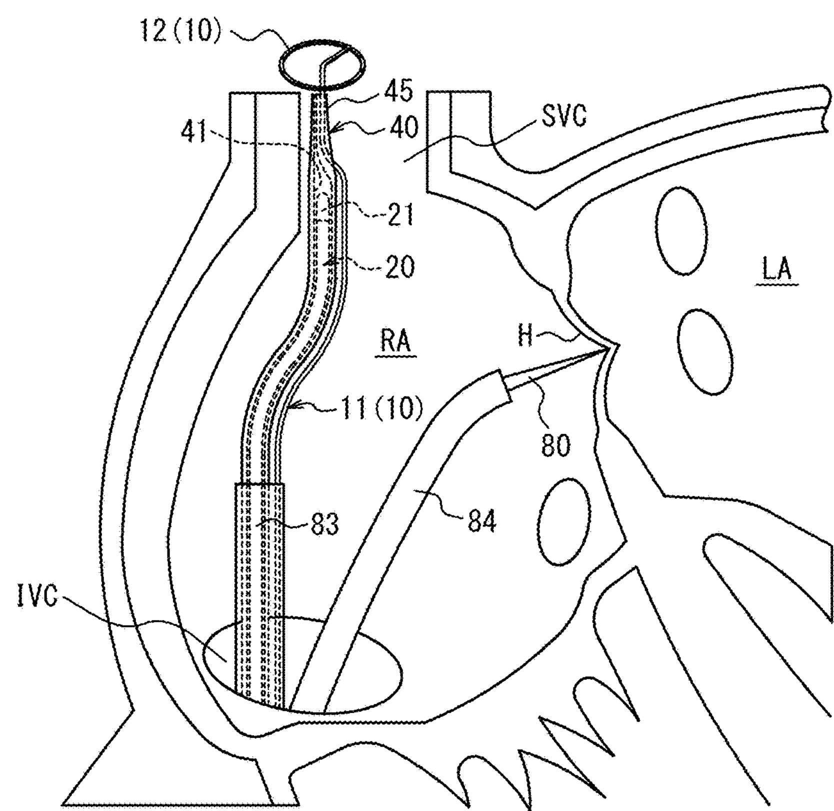
FIG. 7 is a view illustrating a state where a catheter is fixed in a right atrium.

First, a method of acquiring the organ information inside a right atrium which is a lumen of a heart as the organs will be described. FIG. 7 is a view illustrating a state where the catheter 40 is fixed in a right atrium RA. As illustrated in FIG. 7, in the insertion step of Step S10, an operator such as a health care worker inserts the catheter 40 into the right atrium RA through a first sheath 83 from the distal side via an inferior vena cava IVC as a first blood vessel having a diameter smaller than that of the right atrium RA of a subject. At this time, the operator inserts a Brockenbrough needle 80 as a medical instrument into the right atrium RA through a second sheath 84 via the inferior vena cava IVC. The Brockenbrough needle 80 is used to open a left atrium LA from the right atrium RA after penetrating an oval fossa H that separates the right atrium RA and the left atrium LA from each other.

As illustrated in FIG. 7, in the fixing step of Step S20, the operator inserts the distal portion 45 of the catheter 40 into a superior vena cava SVC as a second blood vessel having a diameter smaller than that of the communicating right atrium RA, from the right atrium RA. Specifically, the guide wire 10 can be first inserted into the superior vena cava SVC, and then, the distal portion 45 of the catheter 40 can be inserted into the superior vena cava SVC along the guide wire 10. In this manner, vibration of the distal portion 45 of the catheter 40 is suppressed. Furthermore, the proximal side of the catheter 40 is inserted into the inferior vena cava IVC having the diameter smaller than that of the right atrium RA. Accordingly, the catheter 40 extends over the superior vena cava SVC and the inferior vena cava IVC which have the diameter smaller than that of the right atrium RA. In this manner, the vibration and the movement of a portion of the catheter 40 located inside the right atrium RA are suppressed. In addition, a portion of the catheter 40 located inside the right atrium RA is bent. In this manner, the first lumen 41 through which the ultrasound element 21 passes can be bent. Since the first lumen 41 is bent in this way, it is possible to change a passing position of the ultrasound element 21 when the ultrasound element 21 moves along the extending direction of the catheter 40. Accordingly, for example, the ultrasound element 21 can be closer to a site to be particularly observed on the inner wall surface of the organs (for example, the oval fossa H of the heart). In addition, the annular expansive portion 12 located in the distal end of the guide wire 10 having the diameter larger than that of the distal portion 45 of the catheter 40 is inserted into the superior vena cava SVC. In this manner, the position of the distal portion 45 of the catheter 40 can be further fixed.

As illustrated in FIG. 7, in the information acquisition step of Step S30, in a state where the vibration and the movement of the portion of the catheter 40 located inside the right atrium RA is suppressed, while the ultrasound element 21 is moved inside the first lumen 41 of the catheter 40, the ultrasound element 21 acquires the peripheral information on the organs on the inner wall surface of the right atrium RA. Then, the control unit 54 sequentially generates the two-dimensional images, based on the peripheral information acquired by the ultrasound element 21, and generates the organ position information on the inner wall surface of the right atrium RA, based on the two-dimensional images. In this way, the ultrasound element 21 is moved inside the catheter 40 in a state where the vibration and the movement of the portion of the catheter 40 located inside the right atrium RA are suppressed. Accordingly, the ultrasound element 21 is stably rotated even when the ultrasound element 21 is rotated along the circumferential direction of the catheter 40. The ultrasound element 21 stably moves even when the ultrasound element 21 is moved along the extending direction of the catheter 40. Therefore, it is possible to stably acquire the organ position information on the inner wall surface of the right atrium RA. In the information acquisition step of Step S30, the ultrasound element 21 also acquires information on the instrument of the Brockenbrough needle 80 as a medical instrument. In this case, the storage unit 53 frequently stores the two-dimensional image generated by the control unit 54 when the ultrasound element 21 moves along the extending direction of the catheter 40, and a position of the ultrasound element 21 at that time.

Figure 8:
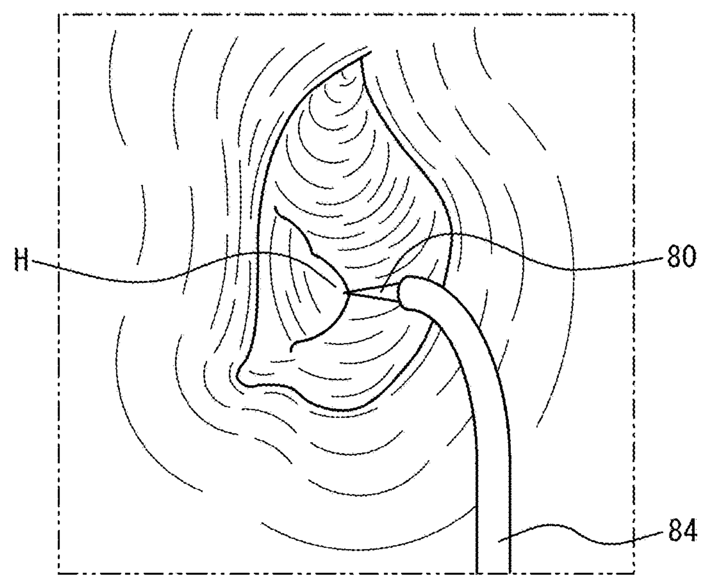
FIG. 8 is a view illustrating a three-dimensional image of the organs which is obtained in a state illustrated in FIG. 7.

The control unit 54 uses the information stored in the storage unit 53, and generates the three-dimensional image of the organs (here, the right atrium RA of the heart) from the organ position information on the inner wall surface of the right atrium RA which is acquired in the information acquisition step of Step S30, and the position and the area of the ultrasound element 21 when the organ position information is acquired. FIG. 8 is a view illustrating the three-dimensional image of the heart as the organs which is acquired in a state illustrated in FIG. 7. As illustrated in FIG. 8, the three-dimensional image including the oval fossa H which is a target site to be penetrated by the Brockenbrough needle 80, on the inner wall surface of the right atrium RA is acquired. Details of the method of generating the three-dimensional image of the organs will be described later.

The organ information acquisition method may further include an adjustment step. As illustrated in FIG. 7, in the adjustment step, the operator deforms the catheter 40 while maintaining a state where the distal portion 45 of the catheter 40 is inserted into the superior vena cava SVC as the second blood vessel, and changes a movement path of the ultrasound element 21. For example, when the operator pushes the catheter 40, a shape of a path of the first lumen 41 of the catheter 40 is changed due to the deformation of the catheter 40. The ultrasound element 21 moves inside the first lumen 41. Accordingly, when the shape of the path of the first lumen 41 is changed, the movement path of the ultrasound element 21 is also changed. In this manner, the peripheral information on the inner wall surface of the right atrium RA which is acquired by the ultrasound element 21 is changed. Accordingly, the three-dimensional image of the organs (here, the right atrium RA of the heart) which is generated based on the peripheral information is also changed. Therefore, for example, even in a case where the Brockenbrough needle 80 as the medical instrument is hidden by the second sheath 84 and the like and is not displayed on the three-dimensional image, the operator further pushes the catheter 40. In this manner, the Brockenbrough needle 80 can be displayed on the three-dimensional image.

Figure 9:
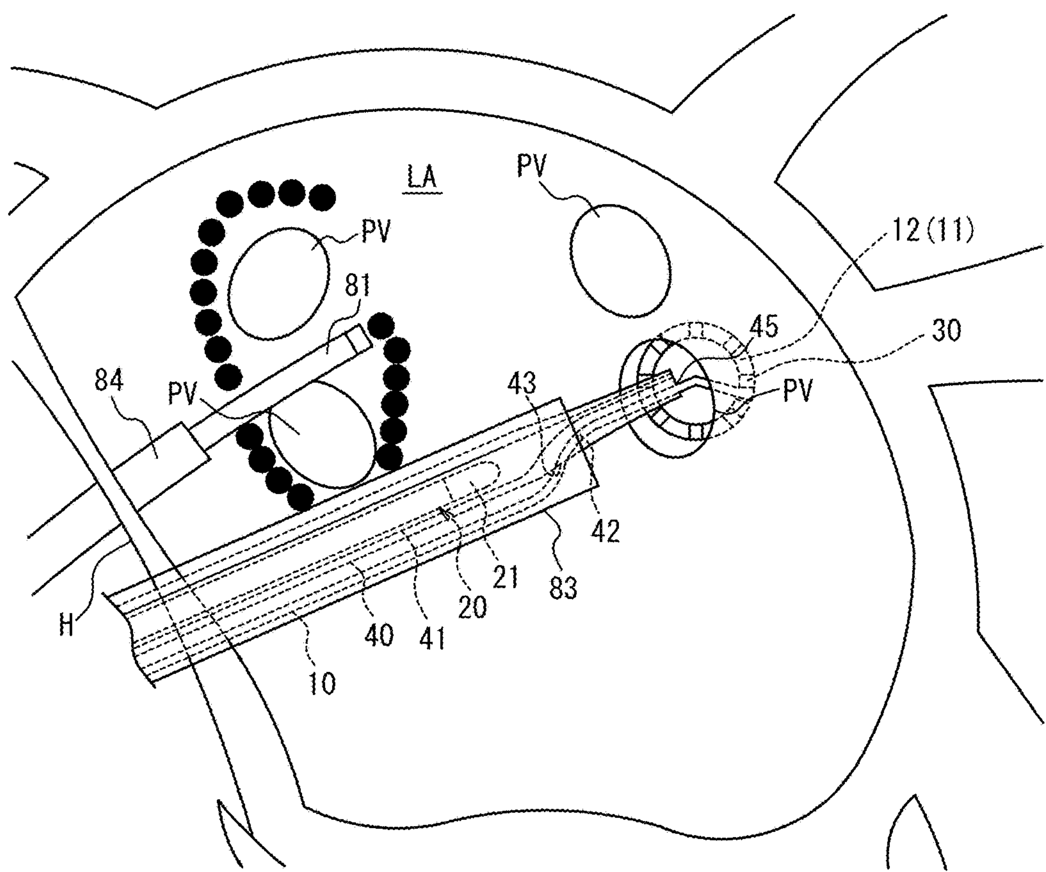
FIG. 9 is a view illustrating a state where the catheter is fixed in a left atrium.

Next, a method of acquiring the organ position information inside the left atrium as the lumen of the heart as the organs will be described. FIG. 9 is a view illustrating a state where the catheter 40 is fixed in the left atrium LA. As illustrated in FIG. 9, in the insertion step of Step S10, the operator inserts the catheter 40 into the left atrium LA through the first sheath 83 from the distal side of the catheter 40 via the inferior vena cava IVC (refer to FIG. 7), the right atrium RA (refer to FIG. 7), and the oval fossa H having the diameter smaller than that of the left atrium LA penetrated by the Brockenbrough needle 80. At this time, the operator inserts an ablation catheter 81 as the medical instrument into the left atrium LA through the second sheath 84 via the right atrium RA and the oval fossa H. The ablation catheter 81 is used for performing ablation treatment by cauterizing a periphery of an opening of a pulmonary vein PV.

As illustrated in FIG. 9, in the fixing step of Step S20, the operator inserts the distal portion 45 of the catheter 40 into the pulmonary vein PV as the second blood vessel having the diameter smaller than that of the communicating left atrium LA, from the left atrium LA. Specifically, the guide wire 10 can be first inserted into the pulmonary vein PV, and then, the distal portion 45 of the catheter 40 can be inserted into the pulmonary vein PV along the guide wire 10. In this manner, vibration of the distal portion 45 of the catheter 40 is suppressed. Furthermore, the proximal side of the catheter 40 is inserted into the oval fossa H having the diameter smaller than that of the left atrium LA. Accordingly, the catheter 40 extends over the pulmonary vein PV and the oval fossa H which have the diameter smaller than that of the left atrium LA. In this manner, the vibration and the movement of the portion of the catheter 40 located inside the left atrium LA are suppressed.

As illustrated in FIG. 9, in the information acquisition step of Step S30, in a state where the vibration and the movement of the portion of the catheter 40 located inside the left atrium LA are suppressed, while the ultrasound element 21 is moved inside the first lumen 41 of the catheter 40, the ultrasound element 21 acquires the peripheral information on the inner wall surface of the left atrium LA. Then, the control unit 54 sequentially generates the two-dimensional images, based on the peripheral information, and generates the organ position information on the inner wall surface of the left atrium LA, based on the two-dimensional image. In this way, the ultrasound element 21 is moved inside the catheter 40 in a state where the vibration and the movement of the portion of the catheter 40 located inside the left atrium LA are suppressed. Accordingly, the ultrasound element 21 is stably rotated even when the ultrasound element 21 is rotated along the circumferential direction of the catheter 40. The ultrasound element 21 stably moves even when the ultrasound element 21 is moved along the extending direction of the catheter 40. Therefore, it is possible to stably acquire the organ position information on the inner wall surface of the left atrium LA. In the information acquisition step of Step S30, the ultrasound element 21 also acquires the peripheral information on the ablation catheter 81 as the medical instrument. In this case, the storage unit 53 frequently stores the two-dimensional image generated by the control unit 54 when the ultrasound element 21 moves along the extending direction of the catheter 40, and a position of the ultrasound element 21 at that time.

Figure 10:
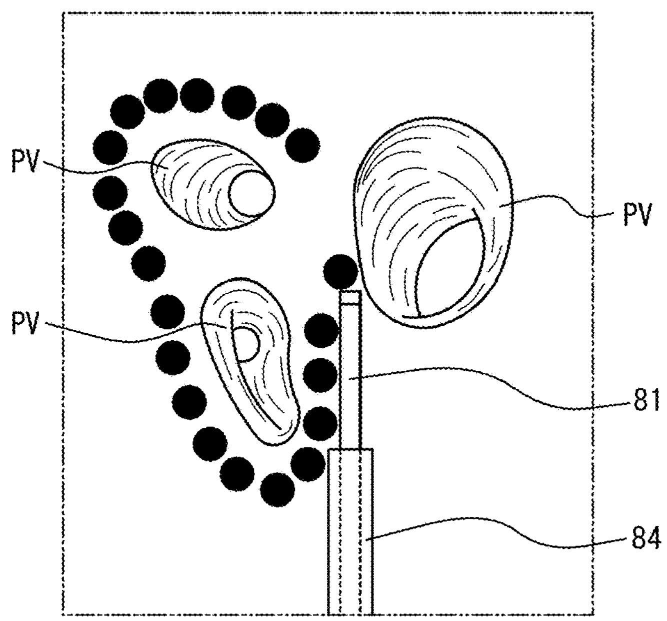
FIG. 10 is a view illustrating a three-dimensional image of the organs which is obtained in a state illustrated in FIG. 9.

The control unit 54 uses the information stored in the storage unit 53, and generates the three-dimensional image of the left atrium LA from the organ position information on the inner wall surface of the left atrium LA which is acquired in the information acquisition step of Step S30, and the position and the area of the ultrasound element 21 when the organ position information is acquired. FIG. 10 is a view illustrating the three-dimensional image of the left atrium LA which is acquired in a state illustrated in FIG. 9. As illustrated in FIG. 10, the three-dimensional image including the periphery of the opening of the pulmonary vein PV which is a target site to be cauterized by the ablation catheter 81 is acquired from the inner wall surface of the left atrium LA.

Incidentally, the organ information acquisition method may further include a re-fixing step. As illustrated in FIGS. 7 and 9, in the re-fixing step, while the operator maintains a state where the catheter 40 is inserted into the right atrium RA as the lumen of the heart via the inferior vena cava IVC as the first blood vessel, the operator removes the distal portion 45 from the superior vena cava SVC as the second blood vessel, and inserts the distal portion 45 into the communicating pulmonary vein PV as the third blood vessel via the oval fossa H, from the right atrium RA. Through the re-fixing step, in a case where the organ position information inside the left atrium LA (refer to FIG. 9) is acquired after the organ position information inside the right atrium RA (refer to FIG. 7) is acquired, the process can be smoothly shifted from the operation of acquiring the organ position information inside the right atrium RA to the operation of acquiring the organ position information inside the left atrium LA.

In a case where the ultrasound element 21 has a plurality of ultrasound transmitters in the direction along the central axis O (refer to FIGS. 3 and 4), when the ultrasound element 21 is rotated along the circumferential direction of the catheter 40, the three-dimensional image illustrated in FIGS. 8 and 10 can be acquired without moving the ultrasound element 21 along the extending direction of the catheter 40. On the other hand, in a case where the ultrasound element 21 has one ultrasound transmitter in the direction along the central axis O, while the ultrasound element 21 is rotated along the circumferential direction of the catheter 40, the ultrasound element 21 is moved along the extending direction of the catheter 40. In this manner, the three-dimensional image illustrated in FIGS. 8 and 10 can be acquired.

[First Display Process]

Figure 11:
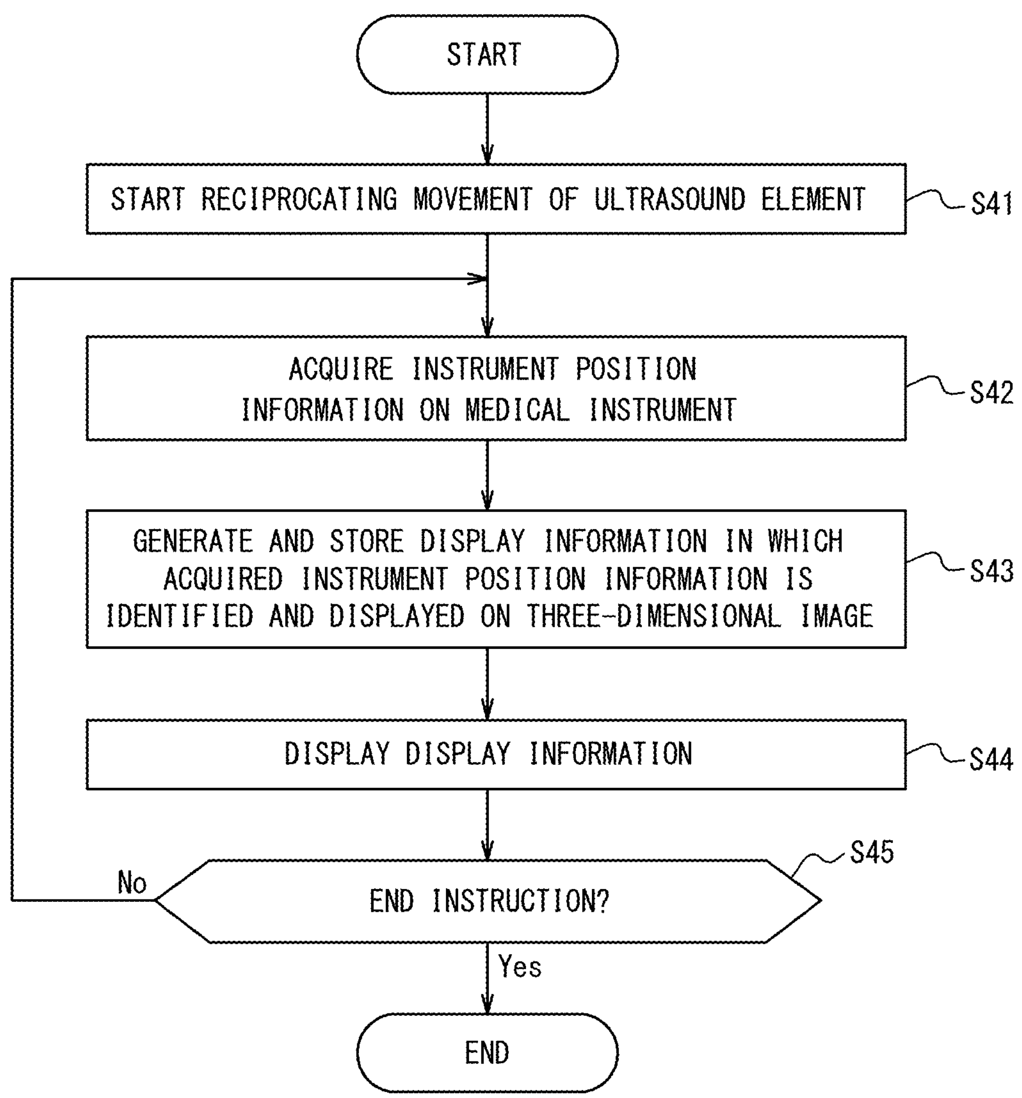
FIG. 11 is a flowchart illustrating a first display process performed by the image processing device.

FIG. 11 is a flowchart illustrating a first display process performed by the image processing device 1. The first display process is performed as a process in the information acquisition step of Step S30 illustrated in FIG. 6. In addition, the image processing device 1 stores the three-dimensional image of the organs of the subject in the storage unit 53 before the first display process is performed.

As illustrated in FIG. 11, for example, when the input unit 52 (refer to FIG. 1 and the like) receives an input of a start instruction, the image processing device 1 starts the ultrasound element 21 (refer to FIG. 3 and the like) to reciprocate (Step S41). Specifically, the ultrasound element 21 starts to reciprocate along the extending direction of the catheter 40 (refer to FIG. 3 and the like) by driving the drive unit 50 (refer to FIG. 2 and the like). Thereafter, the ultrasound element 21 continues to reciprocate until the input unit 52 receives an end instruction in the process of Step S45 (to be described later). In a case where the image processing device 1 stores information on a reciprocating range in the storage unit 53 in advance by performing a first reciprocating range setting process (refer to FIG. 12) or a second reciprocating range setting process (refer to FIG. 13) (to be described later), the image processing device 1 uses the drive unit 50, and causes the ultrasound element 21 to reciprocate within the reciprocating range based on the information on the reciprocating range.

The image processing device 1 uses the control unit 54 to acquire instrument position information on the medical instrument, based on the peripheral information acquired by the ultrasound element 21 (Step S42). Here, the medical instrument is located outside the catheter 40 and within a predetermined range inside the organs. While the ultrasound element 21 reciprocates along the extending direction of the catheter 40, the ultrasound element 21 acquires the peripheral information along a plane orthogonal to the extending direction of the catheter 40. The control unit acquires the instrument position information on the medical instrument, based on the peripheral information.

Thereafter, the image processing device 1 generates and stores the display information in which the acquired instrument position information on the medical instrument is identified and displayed on the three-dimensional image of the organs through superimposed display or the like in real time, that is, during a real time process (Step S43). Specifically, while the ultrasound element 21 reciprocates along the extending direction of the catheter 40, the ultrasound element 21 acquires the peripheral information, and the control unit 54 also acquires the organ position information together with instrument position information, based on the peripheral information. The image processing device 1 reads the three-dimensional image of the organs from the storage unit 53 (refer to FIG. 1 and the like) by using the control unit 54 (refer to FIG. 1 and the like), and specifies each position inside the three-dimensional image which corresponds to the organ position information acquired in a time-dependent manner. Then, the image processing device 1 generates the display information in which the instrument position information on the medical instrument which is acquired in the process of Step S42 is superimposed and displayed on a specified position of the three-dimensional image. Thereafter, the image processing device 1 stores the generated display information in the storage unit 53. At this time, in a case where the display information is previously stored in the storage unit 53, the image processing device 1 stores newly generated display information instead of the previously stored display information. For example, as illustrated in FIG. 7, in a case where the first display process illustrated in FIG. 11 is performed in a state where the catheter 40 is fixed in the right atrium RA, as illustrated in FIG. 8, the display information is generated in which the instrument position information on the Brockenbrough needle 80 as the medical instrument is superimposed on the three-dimensional image of the right atrium RA. In addition, for example, as illustrated in FIG. 9, in a case where the first display process illustrated in FIG. 11 is performed in a state where the catheter 40 is fixed in the left atrium LA, as illustrated in FIG. 10, the display information is generated in which the instrument position information on the ablation catheter 81 as the medical instrument is superimposed on the three-dimensional image of the left atrium LA.

The image processing device 1 displays the generated display information in real time, that is, during a real time process (Step S44). Specifically, the image processing device 1 uses the control unit 54 to read the display information stored in the storage unit 53, and display the display information on the display unit 51 (refer to FIG. 1 and the like). At this time, in a case where the display information is previously displayed on the display unit 51, the image processing device 1 updates the display information by using newly generated display information.

The image processing device 1 determines whether or not the input unit 52 receives the end instruction (Step S45). In a case where the input unit 52 receives the end instruction (Yes in Step S45), the image processing device 1 ends the first display process. On the other hand, in a case where the input unit 52 does not receive the end instruction (No in Step S45), the image processing device 1 returns to the process of Step S42, and acquires the instrument position information on the medical instrument again.

As described above, the ultrasound element 21 reciprocates along the extending direction of the catheter by using the drive unit 50, thereby acquiring time-dependent peripheral information. Furthermore, the control unit 54 acquires time-dependent instrument position information on the medical instrument, based on the peripheral information. Then, the control unit 54 generates the display information in which the time-dependent instrument position information on the medical instrument is identified and displayed inside the three-dimensional image of the organs. In this manner, a time-dependent position of the medical instrument inside the three-dimensional image of the organs can be displayed during the treatment. Accordingly, it is possible to contribute to a proper treatment of the organs.

Figure 12:
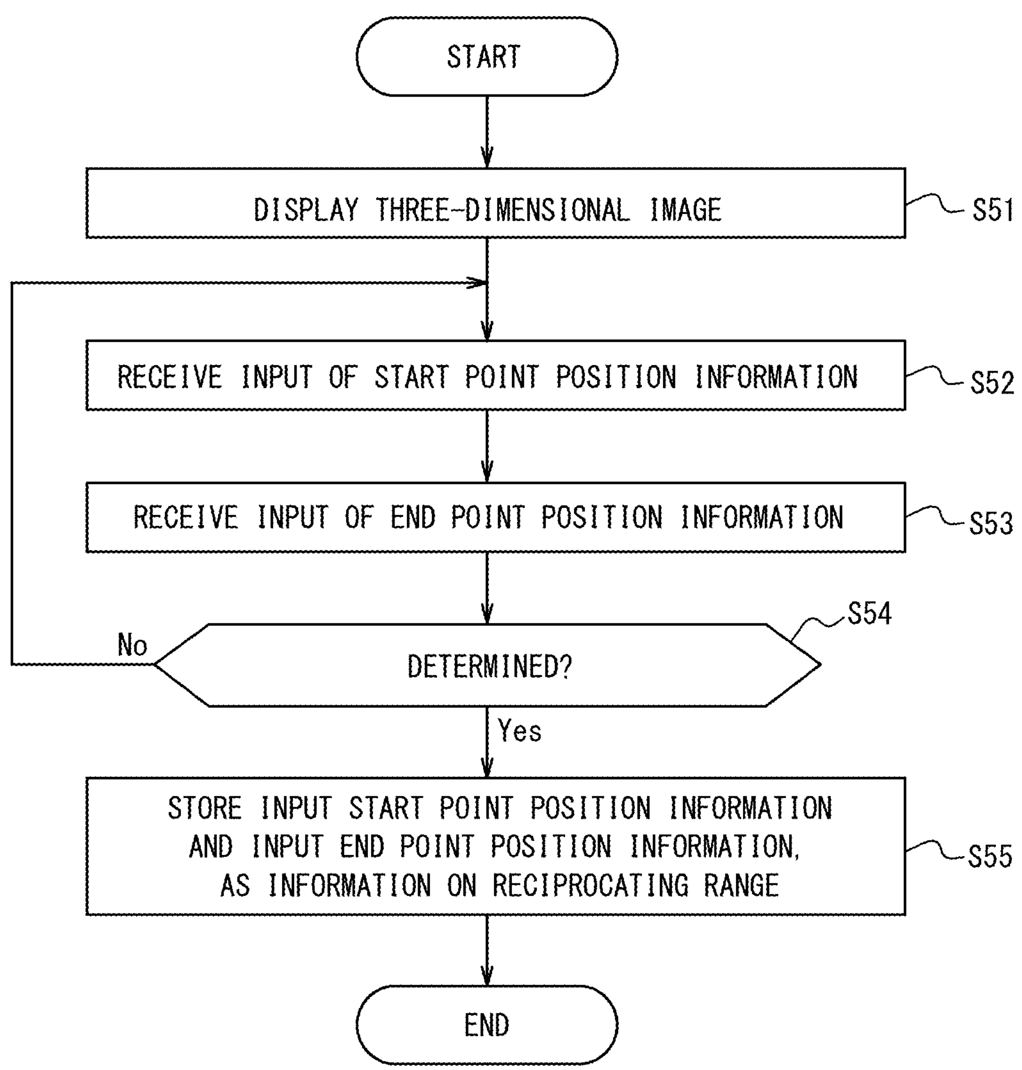
FIG. 12 is a flowchart illustrating a first reciprocating range setting process performed by the image processing device.

FIG. 12 is a flowchart illustrating a first reciprocating range setting process performed by the image processing device 1. The first reciprocating range setting process is performed before the first display process illustrated in FIG. 11 is performed.

As illustrated in FIG. 12, the image processing device 1 displays a three-dimensional image of the organs (Step S51). Specifically, the image processing device 1 uses the control unit 54 (refer to FIG. 1 and the like) to read the three-dimensional image of the organs from the storage unit (refer to FIG. 1 and the like), and display the read three-dimensional image on the display unit 51 (refer to FIG. 1 and the like).

The image processing device 1 uses the input unit 52 (refer to FIG. 1 and the like) to receive an input of start point position information (Step S52). The start point position information is information for designating any desired position of the three-dimensional image of the organs displayed on the display unit 51, as a start point of the reciprocating range of the ultrasound element 21 (refer to FIG. 3 and the like).

The image processing device 1 uses the input unit 52 to receive an input of end point position information (Step S53). Specifically, the end point position information is information for designating any desired position of the three-dimensional image of the organs displayed on the display unit 51, as an end point of the reciprocating range of the ultrasound element 21. For example, the start point position information and the end point position information are input as follows. Any two desired points of the three-dimensional image of the organs displayed on the display unit 51 are designated by using a touch panel disposed integrally with the display unit 51 as the input unit 52 or a mouse as the input unit 52. The process of Step S53 may be performed before the process of Step S52, or may be performed simultaneously with the process of Step S52.

The image processing device 1 uses the control unit 54 to determine whether or not the input unit 52 receives a determination instruction (Step S54). In a case where the input unit 52 receives the determination instruction (Yes in Step S54), the image processing device 1 proceeds to a process in Step S55. On the other hand, in a case where the input unit 52 does not receive the determination instruction (No in Step S54), the image processing device 1 returns to the process of Step S52, and receives the input of the start point position information again.

In a case where the input unit 52 receives the determination instruction (Yes in Step S54), the image processing device 1 stores the input start point position information and the input end point position information in the storage unit 53, as information on the reciprocating range of the ultrasound element 21 (Step S55), and ends the first reciprocating range setting process. Thereafter, the image processing device 1 reads the information on the reciprocating range which is stored in the storage unit 53 in the process of Step S41 of the first display process illustrated in FIG. 11, the image processing device 1 uses the drive unit 50 so that the ultrasound element 21 reciprocates within the reciprocating range based on the information on the reciprocating range.

As described above, while referring to the three-dimensional image, the image processing device 1 can visually set the reciprocating range of the ultrasound element 21 in the first display process illustrated in FIG. 11 by performing a simple operation.

Figure 13:
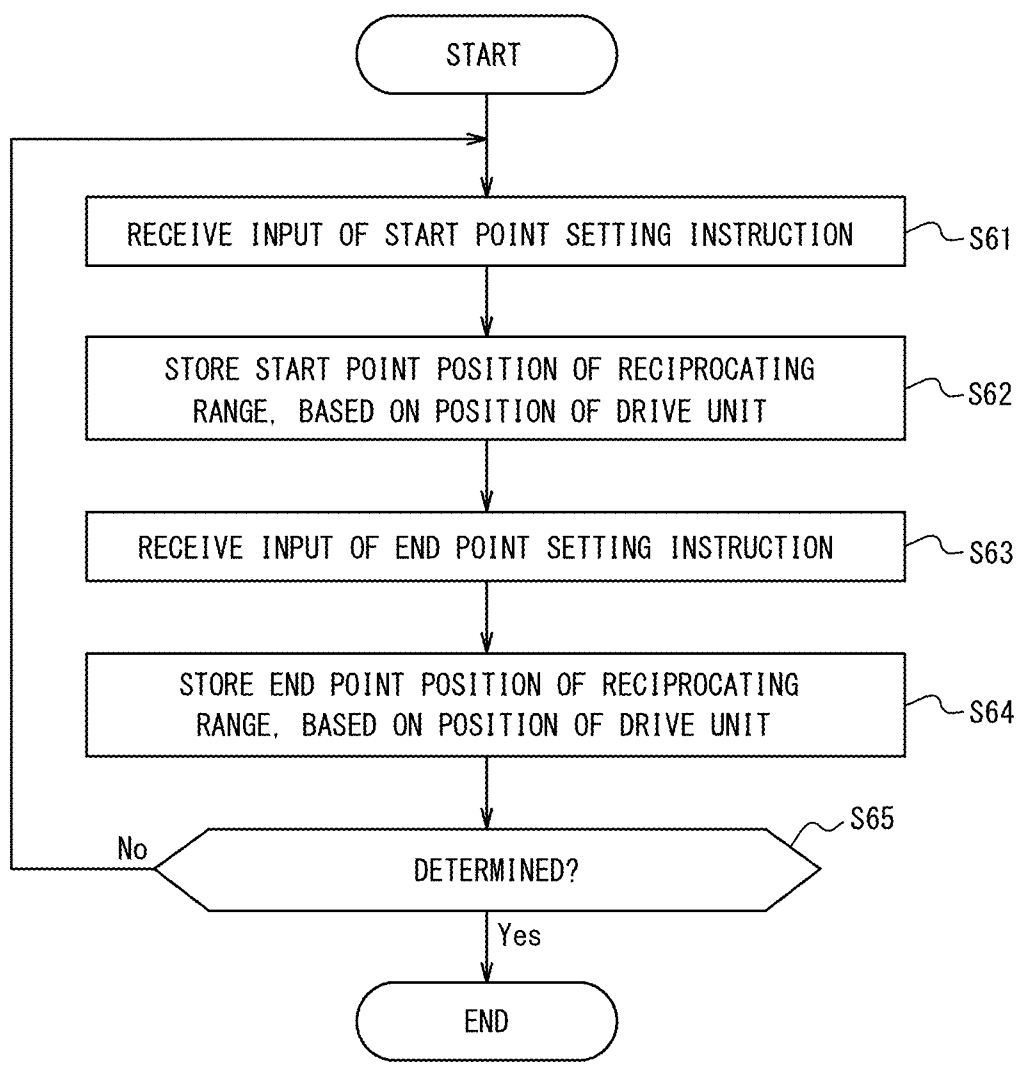
FIG. 13 is a flowchart illustrating a second reciprocating range setting process performed by the image processing device.

FIG. 13 is a flowchart illustrating the second reciprocating range setting process performed by the image processing device 1. The second reciprocating range setting process is performed before the first display process illustrated in FIG. 11 is performed.

As illustrated in FIG. 13, the image processing device 1 uses the input unit 52 (refer to FIG. 1 and the like) to receive an input of a start point setting instruction (Step S61).

The image processing device 1 stores a start point position of the reciprocating range, based on a position of the drive unit 50 (refer to FIG. 2 and the like) when the start point setting instruction is input (Step S62). Here, a position along a reciprocating direction of the shaft 22 (refer to FIG. 4) connecting the drive unit 50 and the ultrasound element 21 (refer to FIG. 3 and the like) with each other is specified from the position of the drive unit when the start point setting instruction is input. Accordingly, it is possible to specify the position of the ultrasound element 21 when the start point setting instruction is input. Therefore, the position of the ultrasound element 21 at that time can be specified, based on the position of the drive unit 50, and the position of the ultrasound element 21 can be set as the start point position of the reciprocating range.

The image processing device 1 uses the input unit 52 to receive an input of an end point setting instruction (Step S63).

The image processing device 1 uses the control unit 54 to store an end point position of the reciprocating range, based on the position of the drive unit 50 when the end point setting instruction is input (Step S64). Here, a position along the reciprocating direction of the shaft 22 connecting the drive unit 50 and the ultrasound element 21 with each other is specified from the position of the drive unit 50 when the end point setting instruction is input. Accordingly, it is possible to specify the position of the ultrasound element 21 when the end point setting instruction is input. Therefore, the position of the ultrasound element 21 at that time can be specified, based on the position of the drive unit 50, and the position of the ultrasound element 21 can be set as the end point position of the reciprocating range.

The image processing device 1 uses the control unit 54 to determine whether or not the input unit 52 receives the determination instruction (Step S65). In a case where the input unit 52 receives the determination instruction (Yes in Step S65), the image processing device 1 ends the second reciprocating range setting process, and stores the information on the reciprocating range in the storage unit 53. On the other hand, in a case where the input unit 52 does not receive the determination instruction (No in Step S65), the image processing device 1 returns to the process of Step S61, and receives the input of the start point setting instruction again. In a case of returning to the process of Step S61, the image processing device 1 stores the information on the reciprocating range which is newly set in the processes of steps S61 to S64 in the storage unit 53, instead of the previously stored information on the reciprocating range. After ending the second reciprocating range setting process, the image processing device 1 reads the information on the reciprocating range stored in the storage unit 53 in the process of Step S41 of the first display process illustrated in FIG. 11, and uses the drive unit 50 so that the ultrasound element 21 reciprocates within the reciprocating range based on the information on the reciprocating range.

As described above, while the image processing device 1 confirms an actually moving distance of the ultrasound element 21, based on the position of the drive unit 50, the image processing device 1 can set the reciprocating range of the ultrasound element 21 in the first display process illustrated in FIG. 11 by performing a simple operation.

[Second Display Process]

Figure 14:
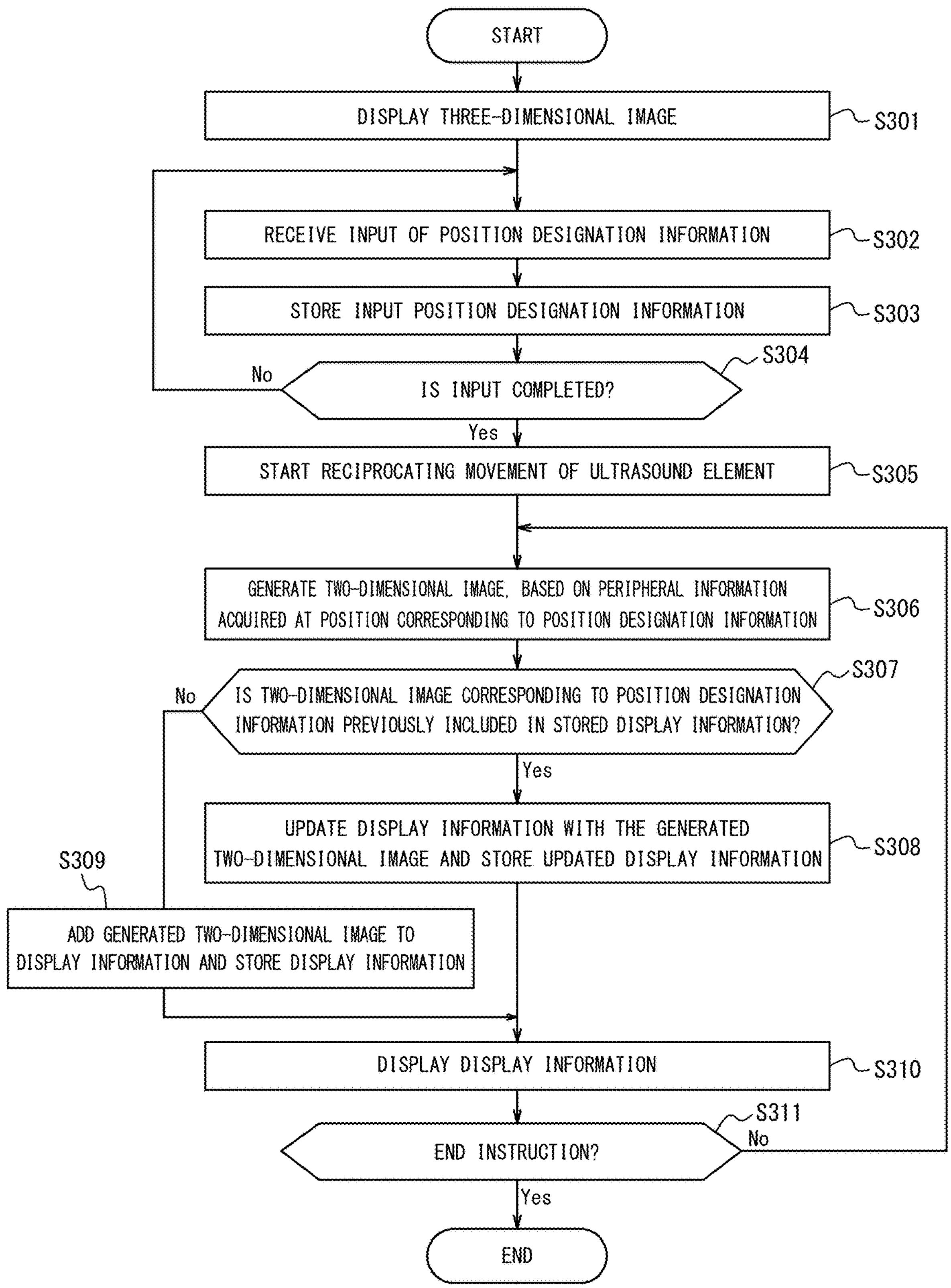
FIG. 14 is a flowchart illustrating a second display process performed by the image processing device.

FIG. 14 is a flowchart illustrating a second display process as a modification example of the first display process (refer to FIG. 11) performed by the image processing device 1. The second display process is performed as a process in the information acquisition step of Step S30 illustrated in FIG. 6. In the second display process, in addition to the display information in the first display process illustrated in FIG. 11, the two-dimensional image showing a cross section at any desired position on the three-dimensional image of the organs of the subject is used as the display information. In addition, the image processing device 1 stores the three-dimensional image of the organs of the subject in the storage unit 53 (refer to FIG. 1 and the like) before the second display process is performed.

As illustrated in FIG. 14, the image processing device 1 displays the three-dimensional image of the organs (Step S301). Specifically, the image processing device 1 uses the control unit 54 (refer to FIG. 1 and the like) to read the three-dimensional image of the organs from the storage unit 53, and display the read three-dimensional image on the display unit 51 (refer to FIG. 1 and the like).

The image processing device 1 uses the input unit 52 (refer to FIG. 1 and the like) to receive an input of position designation information (Step S302). The position designation information is information for designating any desired position of the three-dimensional image of the organs displayed on the display unit 51, as a target of a position for displaying the two-dimensional image showing the cross section.

The image processing device 1 uses the control unit 54 to store the input position designation information in the storage unit 53 (Step S303).

The image processing device 1 uses the control unit 54 to determine whether or not the input unit 52 receives an input end instruction (Step S304). In a case where the input unit 52 receives the input end instruction (Yes in Step S304), the image processing device 1 proceeds to a process in Step S305. On the other hand, in a case where the input unit 52 does not receive the input end instruction (No in Step S304), the image processing device 1 returns to the process of Step S302, and receives the input of the position designation information again. In a case of returning to the process of Step S302, the image processing device 1 stores the position designation information newly set in the processes of Steps S302 and S303 in the storage unit 53, together with the previously stored position designation information. In other words, the image processing device 1 can store a plurality of the position designation information in the storage unit 53.

In the process of Step S305, the image processing device 1 starts the ultrasound element 21 (refer to FIG. 3 and the like) to reciprocate (Step S305). Specifically, the ultrasound element 21 starts to reciprocate along the extending direction of the catheter 40 (refer to FIG. 3 and the like) by driving the drive unit 50 (refer to FIG. 2 and the like). Thereafter, the ultrasound element 21 continues to reciprocate until the input unit 52 receives the end instruction in the process of Step S311 (to be described later). Similarly, until the input unit 52 receives the end instruction in the process of Step S311, the image processing device 1 simultaneously performs the processes of Steps S42 to S44 of the first display process (refer to FIG. 11) in addition to the processes of Steps S306 to S310 (to be described later). In other words, the image processing device 1 displays and updates the three-dimensional image by performing the first display process, in addition to displaying and updating the two-dimensional image by performing the second display process. In addition, in a case where the information on the reciprocating range is stored in the storage unit 53 in advance by performing the above-described first reciprocating range setting process (refer to FIG. 12) or the second reciprocating range setting process (refer to FIG. 13), the image processing device 1 uses the drive unit 50 so that the ultrasound element 21 reciprocates within the reciprocating range based on the information on the reciprocating range.

In the process of Step S306, the image processing device 1 generates the two-dimensional image, based on peripheral position information acquired at a position corresponding to the position designation information. Specifically, first, the image processing device 1 uses the ultrasound element 21 to acquire the peripheral information along a plane orthogonal to the extending direction of the catheter 40 in a time-dependent manner. The image processing device 1 uses the control unit 54 to generate the two-dimensional image, based on the peripheral information acquired by the ultrasound element 21 at the position corresponding to the position designation information. Here, the generated two-dimensional image is a cross-sectional image for the three-dimensional image of the organs along a plane orthogonal to the extending direction of the catheter 40.

The image processing device 1 uses the control unit to determine whether or not the display information stored in the storage unit 53 previously includes the two-dimensional image corresponding to the position designation information (Step S307). The image processing device 1 stores the display information in the storage unit 53 by performing the process of Step S43 in the first display process. In a case where the display information stored in the storage unit 53 does not include the two-dimensional image corresponding to the position designation information (No in Step S307), the image processing device 1 adds a currently generated two-dimensional image to the display information stored in the storage unit 53, and stores the display information in the storage unit 53 (Step S309). On the other hand, in a case where the display information stored in the storage unit 53 previously includes the two-dimensional image corresponding to the position designation information (Yes in Step S307), the image processing device uses the currently generated two-dimensional image to update the two-dimensional image to be included in the display information stored in the storage unit 53, and stores the display information in the storage unit 53 (Step S308).

The image processing device 1 uses the control unit 54 to display the display information stored in the storage unit 53 on the display unit 51 (Step S310).

The image processing device 1 uses the control unit 54 to determine whether or not the input unit 52 receives the end instruction (Step S311). In a case where the image processing device 1 does not receive the end instruction (No in Step S311), the image processing device 1 returns to the process of Step S306. On the other hand, in a case where the image processing device 1 receives the end instruction (Yes in Step S311), the image processing device 1 ends the process according to the modification example of the first display process.

As described above, the image processing device 1 acquires the time-dependent instrument position information on the medical instrument. While the time-dependent instrument position information is superimposed and displayed on the three-dimensional image of the organs, the two-dimensional image showing the cross section at any designated position in the three-dimensional image of the organs can be displayed in a time-dependent manner. Therefore, during the treatment, the time-dependent position of the medical instrument located inside the organs can be displayed on the three-dimensional image and the two-dimensional image. Accordingly, it is possible to further contribute to the proper treatment of the organs.

Figure 15:
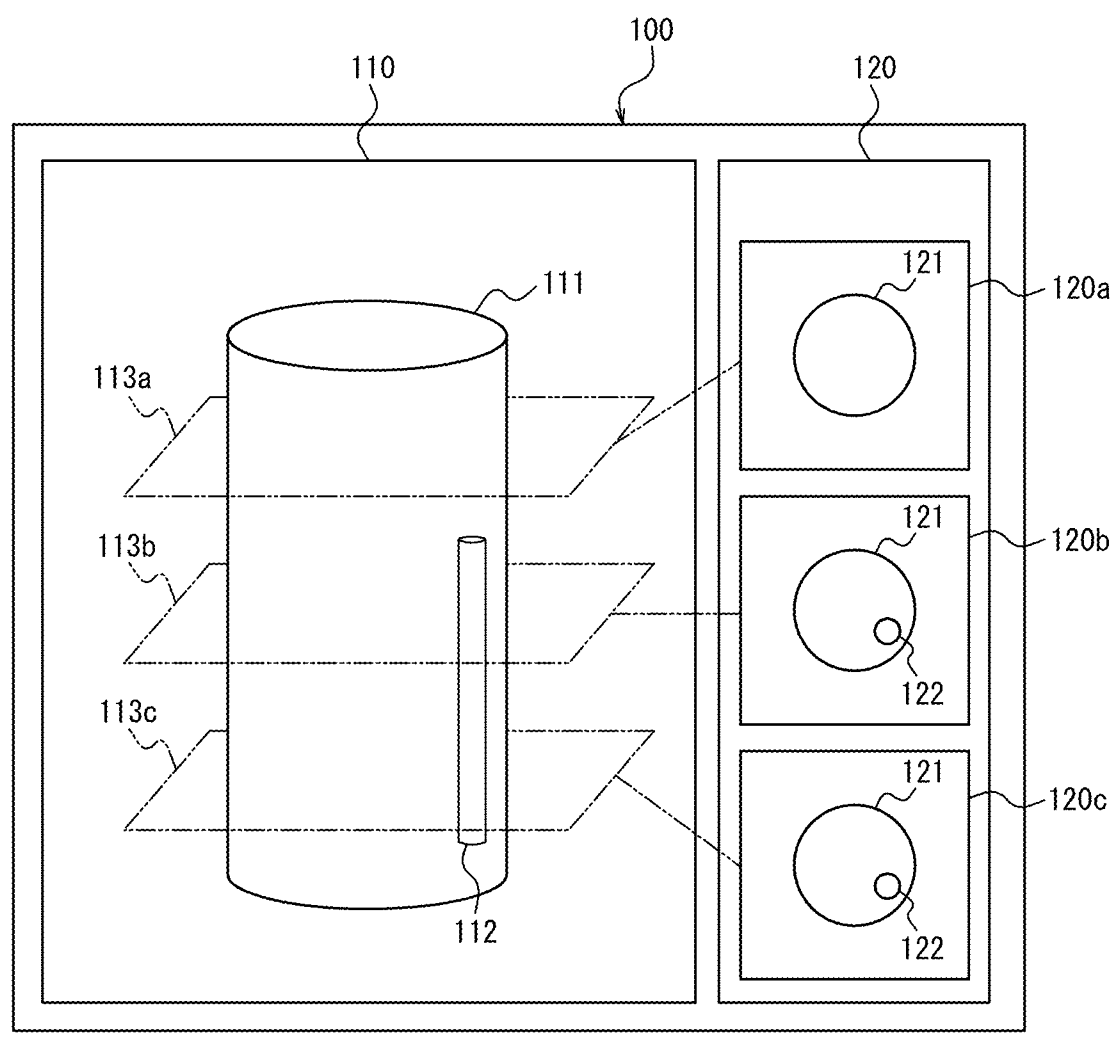
FIG. 15 is a schematic view illustrating an example of display information associated with the second display process.

FIG. 15 is a schematic view illustrating an example of display information associated with the second display process. In FIG. 15, a three-dimensional image 111 of the organs is schematically illustrated by a simple column. As illustrated in FIG. 15, display information 100 includes a three-dimensional image display area 110 and a two-dimensional image display area 120. In the three-dimensional image display area 110, the three-dimensional image 111 of the organs and instrument position information 112 of the medical instrument located inside the organs are illustrated. In addition, in the three-dimensional image display area 110, cross-sectional position information 113*a* to 113*c* serving as information indicating a position designated by the position designation information is illustrated. In the two-dimensional image display area 120, the two-dimensional images generated based on the peripheral position information acquired at the positions corresponding to the cross-sectional position information 113*a* to 113*c* are respectively illustrated in two-dimensional image display areas 120*a* to 120*c*. Specifically, only a two-dimensional image 121 of the organs is illustrated in the two-dimensional image display area 120*a*. In the two-dimensional image display areas 120*b* and 120*c*, the two-dimensional image 121 of the organs and a two-dimensional image 122 of the medical instrument located inside the organs are illustrated. In this way, the two-dimensional image showing the cross section at any designated position in the three-dimensional image of the organs is displayed in a time-dependent manner. Accordingly, when it is determined which two-dimensional image displays the medical instrument, it is possible to easily specify the position of the medical instrument from the positions along the extending direction of the catheter 40.

[Third Display Process]

Hereinafter, a third display process performed by the image processing device 1 will be described. The image processing device 1 stores the three-dimensional image of the organs of the subject in the storage unit 53 (refer to FIG. 1 and the like) in advance before the third display process is performed. In addition, before the third display process is performed, based on the position of the ultrasound element 21 (refer to FIG. 3 and the like) along the extending direction of the catheter 40 (refer to FIG. 3 and the like), the image processing device 1 stores correspondence information capable of specifying a position along a predetermined coordinate axis inside the three-dimensional image of the organs (hereinafter, referred to as "correspondence information" as appropriate) in the storage unit 53 in advance.

For example, the correspondence information is first correspondence information or second correspondence information (to be described later). The first correspondence information includes position correspondence information and correlation position correspondence information. The position correspondence information is information indicating the position of the drive unit 50 (refer to FIG. 2 and the like) which corresponds to the position along the predetermined coordinate axis inside the three-dimensional image of the organs. In other words, the position correspondence information is information indicating the position corresponding to the position along the predetermined coordinate axis inside the three-dimensional image which corresponds to the position of the drive unit 50. For example, the position correspondence information may be information on a combination of the position along the predetermined coordinate axis inside the three-dimensional image of the organs and the position of the drive unit 50. The correlation position correspondence information is information indicating the position of the ultrasound element 21 along the extending direction of the catheter 40 with respect to the position of the drive unit 50. That is, the first correspondence information is information in which the position of the ultrasound element 21 along the extending direction of the catheter 40 and the position along the predetermined coordinate axis inside the three-dimensional image of the organs are associated with each other.

For example, based on the position of the drive unit 50 which is used in the second reciprocating range setting process (refer to FIG. 13), the drive unit 50 (refer to FIG. 2 and the like) can specify the position of the ultrasound element 21 along the extending direction of the catheter 40. In addition, the three-dimensional image of the organs is generated by the drive unit 50, based on the peripheral information acquired while the ultrasound element 21 is moving along the extending direction of the catheter 40. Therefore, when the drive unit 50 moves the ultrasound element 21 to generate the three-dimensional image, the image processing device 1 can generate the correspondence information between the position of the ultrasound element 21 in the extending direction of the catheter 40 and the position along the predetermined coordinate axis inside the three-dimensional image, that is, along the coordinate axis corresponding to the extending direction of the catheter 40, as the first correspondence information.

Figure 16:
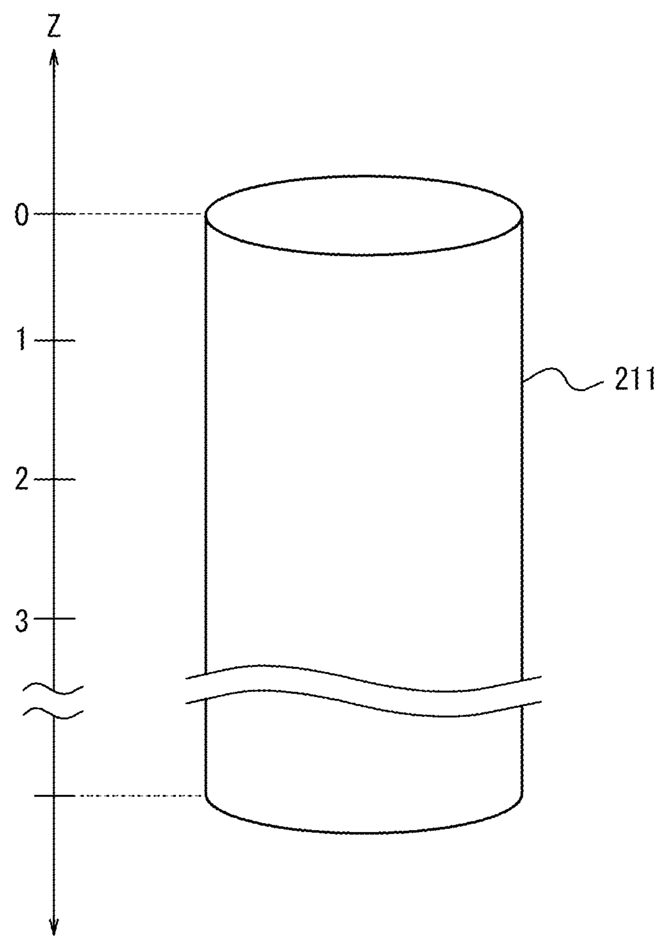
FIG. 16 is a view illustrating an example of a position along a predetermined coordinate axis inside the three-dimensional image.
Figure 17:
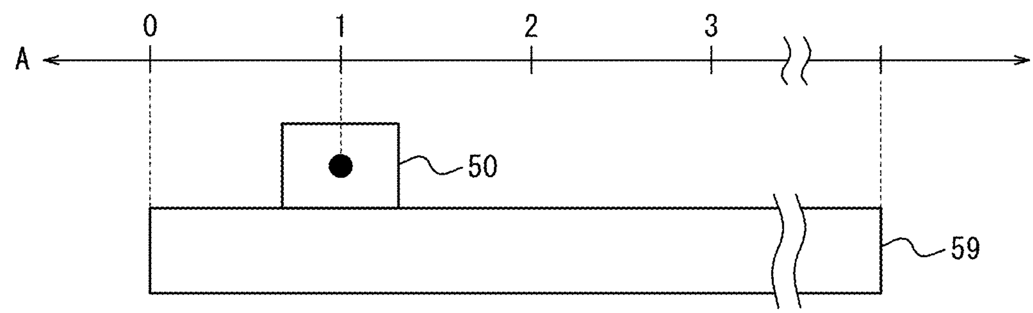
FIG. 17 is a view illustrating an example of a position of a drive unit.

FIG. 16 is a view illustrating an example of positions along a Z-axis as a predetermined coordinate axis inside a three-dimensional image 211 of the organs. In FIG. 16, the three-dimensional image 211 of the organs is schematically illustrated by a simple column. FIG. 17 is a view illustrating an example of the position of the drive unit 50. As illustrated in FIG. 17, the drive unit 50 is movable on the base 59 along an A-axis as a predetermined coordinate axis. In the example illustrated in FIG. 17, a central position of the drive unit 50 is located at a position where A=1 is satisfied along the A-axis as the predetermined coordinate axis.

FIG. 18 is a view illustrating an example of the position correspondence information. As illustrated in FIG. 18, the position correspondence information may be information on a combination in which the position along the Z-axis as the predetermined coordinate axis inside the three-dimensional image 211 of the organs illustrated in FIG. 16 and the position along the A-axis as the predetermined coordinate axis of the drive unit 50 illustrated in FIG. 17 are associated with each other. However, the position correspondence information is not limited to the information on the combination as illustrated in FIG. 18.

The above-described position correspondence information is not limited to the information on the combination of the position along the predetermined coordinate axis inside the three-dimensional image of the organs and the position of the drive unit 50. For example, the position correspondence information may include information on a moving speed of the drive unit 50 and information on a predetermined time interval as a frame rate. In this case, the drive unit 50 moves at the moving speed (constant speed) included in the position correspondence information. Then, based on the ultrasound wave received by the ultrasound element 21 at a current position, the control unit 54 sequentially generates current two-dimensional images showing an inner portion of the organs at a predetermined time interval included in the position correspondence information, and generates serial number information as frame numbers associated with the current two-dimensional images in an ascending order. Thereafter, the control unit 54 can determine the position of the drive unit 50 inside the three-dimensional image of the organs, based on the position correspondence information and the serial number information. The position correspondence information may also include information on an initial position of the drive unit 50.

The second correspondence information includes image correspondence information in which a plurality of the two-dimensional images and the positions along the predetermined coordinate axis inside the three-dimensional image of the organs are associated with each other. Specifically, the plurality of two-dimensional images included in the second correspondence information are generated, based on the peripheral information acquired by the ultrasound element 21 along the extending direction of the catheter 40. Then, the three-dimensional image of the organs is generated, based on the plurality of generated two-dimensional images. Therefore, each of the two-dimensional images is a cross-sectional image configuring a cross-section disposed along the predetermined coordinate axis of the three-dimensional image, which is orthogonal to the predetermined coordinate axis. While the image processing device 1 moves the ultrasound element 21 along the extending direction of the catheter 40, the image processing device 1 can generate second correspondence information including the plurality of two-dimensional images and the information on the positions along a predetermined coordinate axis inside the three-dimensional image of the organs corresponding to the respective two-dimensional images, that is, along a coordinate axis corresponding to the extending direction of the catheter 40.

FIG. 19 is a view illustrating an example of the image correspondence information. As illustrated in FIG. 19, the image correspondence information may be information on a combination in which the position along the Z-axis as the predetermined coordinate axis inside the three-dimensional image 211 of the organs illustrated in FIG. 16 and the cross-sectional image acquired by the ultrasound element at each position and generated by the control unit 54 are associated with each other.

Figure 20:
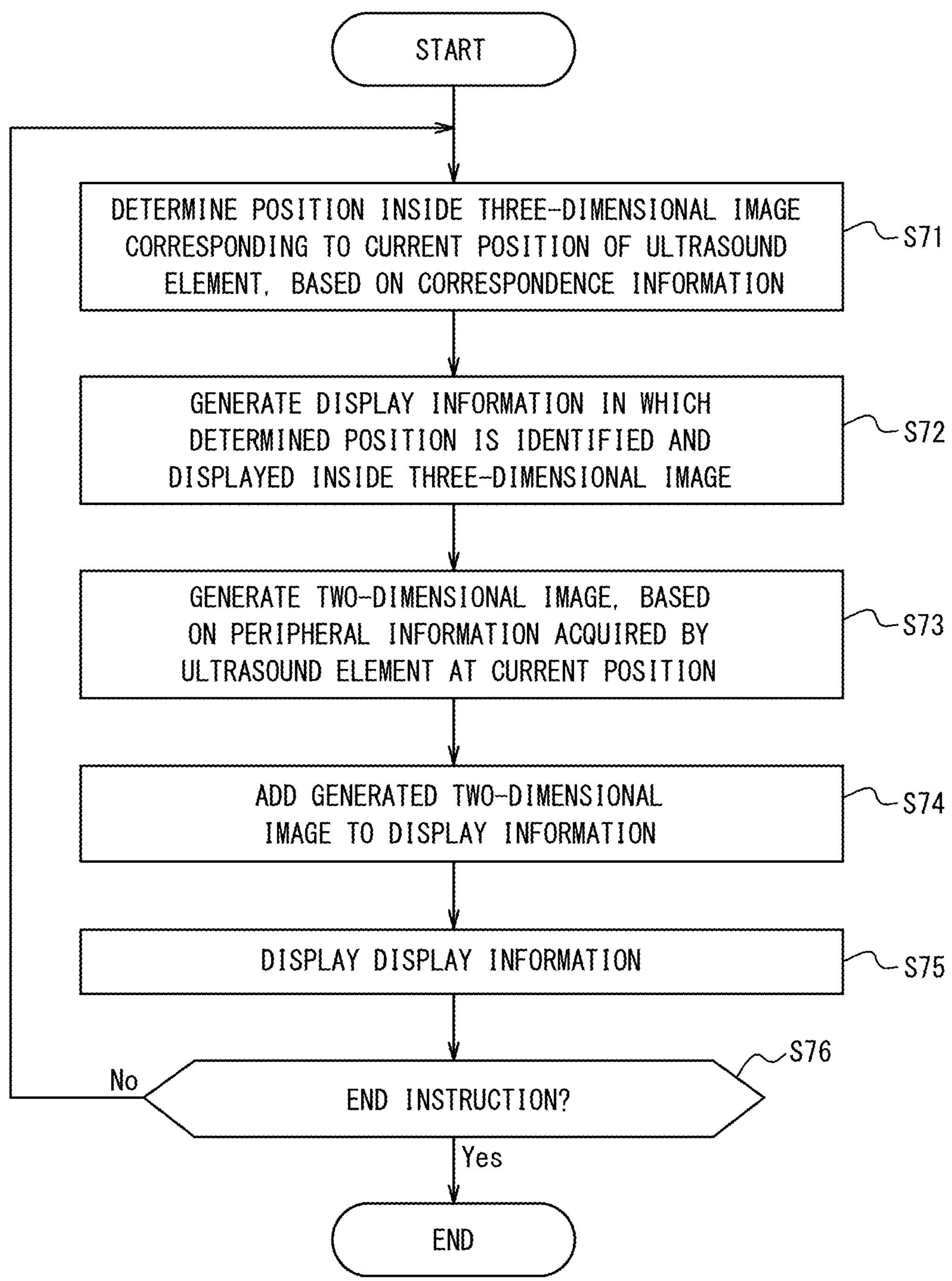
FIG. 20 is a flowchart illustrating a third display process performed by the image processing device.

FIG. 20 is a flowchart illustrating a third display process performed by the image processing device 1. The third display process is performed as a process in the information acquisition step of Step S30 illustrated in FIG. 6.

As illustrated in FIG. 20, the image processing device 1 uses the control unit 54 (refer to FIG. 1 and the like) to determine the position inside the three-dimensional image which corresponds to the current position of the ultrasound element 21, based on the correspondence information stored in the storage unit 53 (Step S71). Specifically, in a case where the correspondence information stored in the storage unit 53 is the first correspondence information, the image processing device 1 uses the control unit 54 to determine the position along the predetermined coordinate axis inside the three-dimensional image, which is specified by the drive unit 50 and corresponds to the current position of the ultrasound element 21 along the extending direction of the catheter 40, based on the first correspondence information.

In addition, in a case where the correspondence information stored in the storage unit 53 is the second correspondence information, the image processing device 1 uses the control unit 54 to generate the current two-dimensional image of the organs, based on the peripheral information acquired by the ultrasound element 21 at the current position. The image processing device 1 extracts the two-dimensional image similar to the generated current two-dimensional image from the plurality of two-dimensional images included in the second correspondence information. The similar two-dimensional images can be extracted by pattern recognition, for example. Then, the image processing device 1 reads the position inside the three-dimensional image corresponding to the extracted two-dimensional image, from the second correspondence information, and determines the read position as the position inside the three-dimensional image which corresponds to the current position of the ultrasound element 21.

The image processing device 1 uses the control unit to generate the display information in which the determined position is identified and displayed inside the three-dimensional image (Step S72).

The image processing device 1 uses the control unit to generate the current two-dimensional image of the organs, based on the peripheral information acquired by the ultrasound element 21 at the current position (Step S73). Here, the generated two-dimensional image is a cross-sectional image for the three-dimensional image of the organs along a plane orthogonal to the extending direction of the catheter 40.

The image processing device 1 uses the control unit 54 to add the generated two-dimensional image to the display information (Step S74). At this time, in a case where the two-dimensional image added to the display information is previously present, the image processing device 1 adds the currently generated two-dimensional image to the display information, instead of the previously generated two-dimensional image.

The image processing device 1 uses the control unit 54 to display the display information stored in the storage unit 53 on the display unit 51 (refer to FIG. 1 and the like) (Step S75). At this time, in a case where the display information is previously displayed on the display unit 51, the image processing device 1 updates the display information by using newly generated display information.

The image processing device 1 uses the control unit 54 to determine whether or not the input unit 52 (refer to FIG. 1 and the like) receives the end instruction (Step S76). In a case where the image processing device 1 does not receive the end instruction (No in Step S76), the image processing device 1 returns to the process of Step S71. On the other hand, in a case where the image processing device 1 receives the end instruction (Yes in Step S76), the image processing device 1 ends the third display process.

Figure 21:
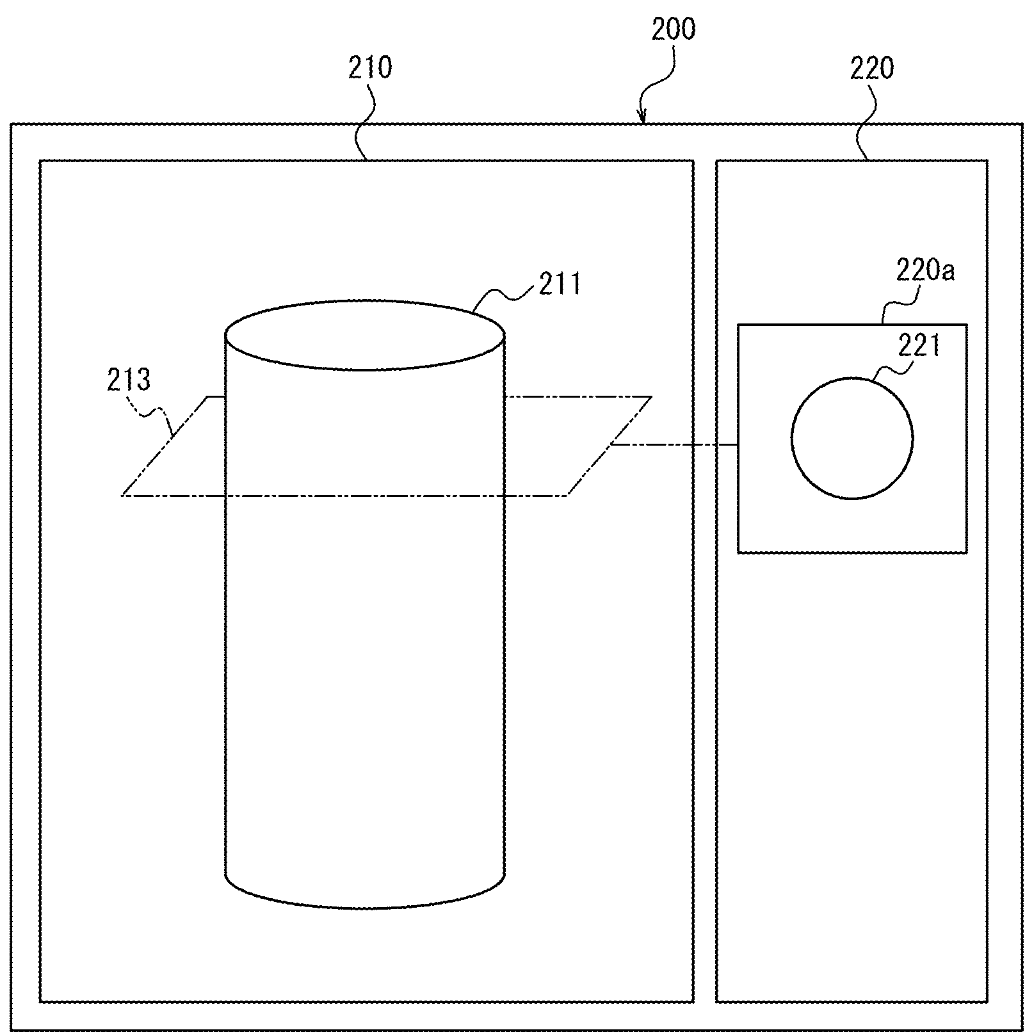
FIG. 21 is a schematic view illustrating an example of display information associated with the third display process.
Figure 22:
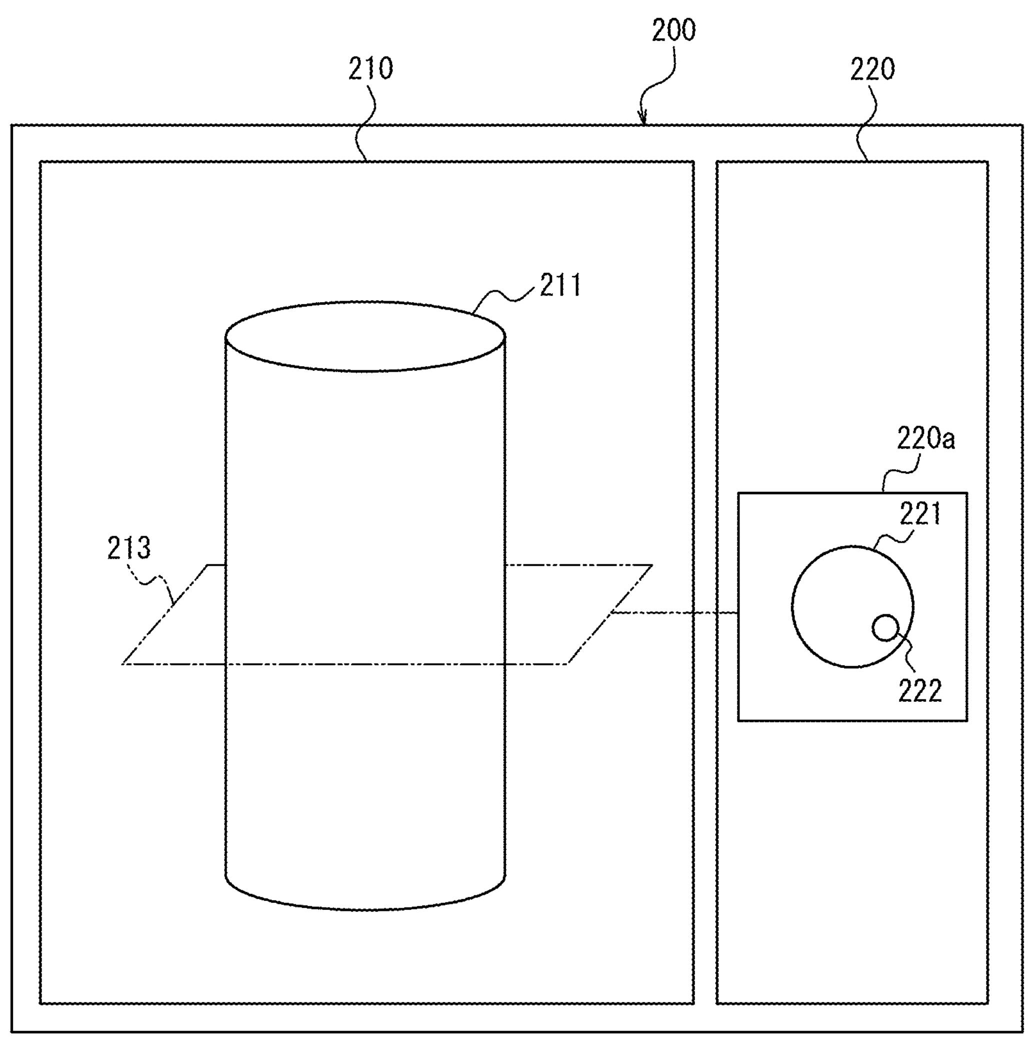
FIG. 22 is a schematic view illustrating an example of the display information associated with the third display process.

FIGS. 21 and 22 are schematic views illustrating an example of display information associated with the third display process at mutually different times. In FIGS. 21 and 22, the three-dimensional image 211 of the organs is schematically illustrated by a simple column. As illustrated in FIGS. 21 and 22, display information 200 includes a three-dimensional image display area 210 and a two-dimensional image display area 220. In the three-dimensional image display area 210, the three-dimensional image 211 of the organs is illustrated. In addition, in the three-dimensional image display area 210, ultrasound element position information 213 indicating a position determined as the position inside the three-dimensional image 211 which corresponds to the current position of the ultrasound element 21 is illustrated. In the two-dimensional image display area 220, the two-dimensional image generated based on the peripheral information acquired at the current position of the ultrasound element 21 which corresponds to the ultrasound element position information 213 is illustrated. Specifically, only a two-dimensional image 221 of the organs is illustrated in a two-dimensional image display area 220*a* illustrated in FIG. 21. In a two-dimensional image display area 220*b* illustrated in FIG. 22, the two-dimensional image 221 of the organs and a two-dimensional image 222 of the medical instrument located inside the organs are illustrated.

As described above, the position inside the three-dimensional image of the organs which corresponds to the current position of the ultrasound element 21 can be identified and displayed inside the three-dimensional image. Accordingly, the image processing device 1 can easily recognize the position of the ultrasound element 21 inside the three-dimensional image of the organs. In addition, the image processing device 1 can display the two-dimensional image generated based on the peripheral information acquired at the current position of the ultrasound element 21. Accordingly, even in a case where the medical instrument located inside the organs is not included in the previously generated three-dimensional image of the organs or even in a case where the medical instrument is less likely to be visually recognized from the previously generated three-dimensional image, the position of the medical instrument can be easily specified at the position along the extending direction of the catheter 40.

The present disclosure is not limited to the configurations specified in the above-described respective embodiments, and various modifications can be made within the scope not departing from the gist of the invention disclosed in the appended claims. For example, functions included in each configuration element and each step can be rearranged so that all of these do not logically contradict each other. A plurality of the configuration elements or the steps can be combined into one, or can be divided.

In the above-described embodiment, a configuration has been described in which the ultrasound element 21 of the ultrasound tester 20 is used as the peripheral information acquisition device. However, the invention is not limited to this configuration. For example, an apparatus including an image sensor element as the peripheral information acquisition device may be used instead of the ultrasound tester 20. Examples of the apparatus using the image sensor element include an optical coherence tomography apparatus, an optical frequency domain imaging apparatus for diagnosis, or an endoscope. In a case of using the optical coherence tomography apparatus or the optical frequency domain imaging apparatus for diagnosis, an imaging core unit that emits light toward the periphery to detect the reflected light can be used as the image sensor element. In a case of using the endoscope, a light-receiving element such as a CCD sensor or a CMOS sensor that receives light from a subject and converts the light into an electric signal corresponding to intensity of the light can be used as the image sensor element.

As described above, the image processing device 1 as an embodiment of the image processing device according to the present disclosure includes the drive unit 50 and the image processing unit 60 (refer to FIG. 1).

The drive unit 50 is connected with the ultrasound element 21 or the image sensor element which is located inside the catheter 40 as a tubular member, transmits the ultrasound wave or the light, and receives the ultrasound wave or the light reflected from the organ, the blood vessel, or the medical instrument (refer to FIGS. 2 and 3 and the like).

The image processing unit 60 converts the information received by the ultrasound element 21 or the image sensor element (hereinafter, referred to as "reception information") into an electric signal, and sequentially generates the two-dimensional images of the organ, the blood vessel, or the medical instruments. The image processing unit 60 superimposes the generated two-dimensional images one on another, and can generate the three-dimensional image of the organ, the blood vessel, or the medical instrument.

Furthermore, as described above, the drive unit 50 can move the ultrasound element 21 or the image sensor element along the extending direction of the catheter 40 as the tubular member.

In addition, the image processing unit 60 includes the storage unit 53 and the control unit 54 (refer to FIG. 1).

The storage unit 53 can store the position correspondence information in which the position of the drive unit 50 and the position along the predetermined coordinate axis inside the three-dimensional image are associated with each other, and/or the image correspondence information in which the position along the predetermined coordinate axis inside the three-dimensional image and the position of the two-dimensional images superimposed along the predetermined coordinate axis are associated with each other.

As described above, the position correspondence information is information indicating the position of the drive unit 50 which corresponds to the position along the predetermined coordinate axis inside the three-dimensional image of the organs. The information in which the position of the drive unit 50 and the position along the predetermined coordinate axis inside the three-dimensional image are associated with each other is an example of the above-described position correspondence information.

As described above, the image correspondence information is information in which the plurality of two-dimensional images and the positions along the predetermined coordinate axis inside the three-dimensional image of the organs are associated with each other. The information in which the position along the predetermined coordinate axis inside the three-dimensional image and the position of the two-dimensional images superimposed along the predetermined coordinate axis are associated with each other is an example of the above-described image correspondence information.

The control unit 54 can determine the position inside the three-dimensional image which corresponds to the current position of the ultrasound element 21 or the image sensor element, based on the position correspondence information or the image correspondence information. In addition, the control unit 54 can generate the display information in real time, in which the determined position inside the three-dimensional image is identified and displayed inside the three-dimensional image.

More specifically, the control unit 54 may adopt the following procedure as an example of a determination method based on the above-described image correspondence information.

(I) The ultrasound element 21 or the image sensor element converts the reception information acquired at the current position into the electric signal to generate the two-dimensional image at the current position.

(II) The generated two-dimensional image at the current position is compared with the plurality of two-dimensional images superimposed on the previously generated three-dimensional image.

(III) The two-dimensional image similar to the generated two-dimensional image at the current position is extracted from the plurality of superimposed two-dimensional images.

(IV) The position along the predetermined coordinate axis of the three-dimensional image in the extracted two-dimensional image is determined as the position along the predetermined coordinate axis of the three-dimensional image in the generated two-dimensional image at the current position.

The control unit 54 may determine the position inside the three-dimensional image corresponding to the current position of the ultrasound element 21 or the image sensor element through the above-described procedures (I) to (IV).

Here, "similarity" in (III) above means that a coincidence degree between the two two-dimensional images to be compared with each other is 90% or higher, for example.

Furthermore, the storage unit 53 may store the correlation position correspondence information in addition to the above-described position correspondence information. As described above, the correlation position correspondence information is information indicating the position of the ultrasound element 21 or the image sensor element with respect to the position of the drive unit 50. As an example of the correlation position correspondence information, for example, the storage unit 53 can store the information in which the position of the drive unit 50 and the position of the ultrasound element 21 or the image sensor element are associated with each other. An example of the correlation position correspondence information can be acquired by specifying the position of the ultrasound element 21 or the image sensor element in the extending direction of the catheter 40 as the tubular member, for example, based on the position of the drive unit 50 in the extending direction of the catheter 40 as the tubular member.

As described above, the control unit 54 may determine the position inside the three-dimensional image which corresponds to the current position of the ultrasound element 21 or the image sensor element, based on the above-described position correspondence information and the above-described correlation position correspondence information.

Finally, an image display method performed by the image processing device 1 as an embodiment of the image processing device according to the present disclosure will be described.

As described above, the image processing unit 60 of the image processing device 1 includes the display unit 51 (refer to FIGS. 1 and 2).

As described above, the display unit 51 can display the three-dimensional image, the cross-sectional position information on the three-dimensional image, and the two-dimensional image at the position corresponding to the cross-sectional position information (refer to FIGS. 15, 21, and 22).

The display unit 51 can simultaneously display the three-dimensional image, the cross-sectional position information, and the two-dimensional image (refer to FIGS. 15, 21, and 22).

More specifically, as illustrated in FIG. 15, the display unit 51 may display the plurality of cross-sectional position information at different positions along the predetermined coordinate axis of the three-dimensional image, as the cross-sectional position information on the three-dimensional image. In addition, as illustrated in FIG. 15, the display unit 51 may display the plurality of two-dimensional images respectively corresponding to the plurality of cross-sectional position information, as the two-dimensional image.

Furthermore, as illustrated in FIGS. 21 and 22, the display unit 51 may display the current position of the ultrasound transducer 21 or the image sensor element on the three-dimensional image (refer to the reference numeral "213" in FIGS. 21 and 22).

INDUSTRIAL APPLICABILITY

The present disclosure relates to an image processing device and an image display method.

REFERENCE SIGNS LIST

1: image processing device
2: medical device
10: guide wire
11: linear portion
12: annular expansive portion
13: distal end of annular expansive portion
20: ultrasound tester
21: ultrasound element (position acquisition unit)
22: shaft
23: tube
30, 30*a* to 30*j*: electrode
40: catheter (tubular member)
41: first lumen
42: second lumen
43: proximally located side communication hole
44: distally located side communication hole
45: distal portion
46: opening
50: drive unit
51: display unit
52: input unit
53: storage unit
54: control unit
55: Information input unit
59: base
60: image processing unit
80: Brockenbrough needle (medical instrument)
81: ablation catheter (medical instrument)
83: first sheath
84: second sheath
100: display information
110: three-dimensional display area
111: three-dimensional image of organs
112: instrument position information
113*a*, 113*b*, 113*c*: cross-sectional position information
120, 120*a*, 120*b*, 120*c*: two-dimensional display area
121: two-dimensional image of organs
122: two-dimensional image of medical instrument
200: display information
210: three-dimensional image display area
211: three-dimensional image of organs
213: ultrasound element position information
220, 220*a*, 220*b*: two-dimensional image display area
221: two-dimensional image of organs
222: two-dimensional image of medical instrument
A: radial direction of guide wire
B: circumferential direction of guide wire
O: central axis of ultrasound tester
H: oval fossa
IVC: inferior vena cava
SVC: superior vena cava
PV: pulmonary vein
LA: left atrium
RA: right atrium

The invention claimed is:

1. An image processing device comprising:

a motor that is connected with a peripheral information acquisition device located inside a tubular member and is configured to move the peripheral information acquisition device along an extending direction of the tubular member, the peripheral information acquisition device being configured to emit an ultrasound wave or light toward a periphery of the tubular member inside an organ or a blood vessel and acquire a reflected ultrasound wave or reflected light as peripheral information;

a memory; and a processor configured to:

sequentially generate two-dimensional images based on the peripheral information acquired by the peripheral information acquisition device;

generate a three-dimensional image of the organ or the blood vessel based on the two-dimensional images sequentially generated;

store, in the memory, position correspondence information indicating respective positions along a predetermined coordinate axis inside the three-dimensional image that correspond to positions of the motor or image correspondence information associating the respective positions along the predetermined coordinate axis inside the three-dimensional image with the two-dimensional images sequentially generated;

determine a position, from among the respective positions along the predetermined coordinate axis inside the three-dimensional image, corresponding to a current position of the peripheral information acquisition device based on the position correspondence information or the image correspondence information stored in the memory;

generate, in real time, display information including a first display area in which a two-dimensional image generated based on the peripheral information acquired by the peripheral information acquisition device at the current position is displayed, and a second display area in which the determined position corresponding to the current position of the peripheral information acquisition device is identified and displayed along with the three-dimensional image; and update, in a case where the display information is previously displayed and the peripheral information acquisition device has moved, the display information such that a newly determined position corresponding to a position to which the peripheral information acquisition device has moved is identified and displayed in the second display area while a two-dimensional image generated based on the peripheral information acquired by the peripheral information acquisition device at the position to which the peripheral information acquisition device has moved is displayed in the first display area.

2. The image processing device according to claim 1, wherein the memory is configured to store the position correspondence information and correlation position correspondence information indicating a corresponding position of the peripheral information acquisition device with respect to each of the positions of the motor, and wherein the processor is configured to determine the position corresponding to the current position of the peripheral information acquisition device, which is specified by a current position of the motor, based on the position correspondence information and the correlation position correspondence information.

3. The image processing device according to claim 2, wherein the motor is configured to move at a constant speed, wherein the processor is configured to sequentially generate the two-dimensional images at a predetermined time interval, and generate serial number information associated with the two-dimensional images sequentially generated in an ascending order, and wherein the position correspondence information includes information on a moving speed of the motor and information on the predetermined time interval.

4. The image processing device according to claim 1, wherein the memory is configured to store the image correspondence information, and wherein the processor is configured to extract, from among the two-dimensional images sequentially generated, a two-dimensional image similar to the two-dimensional image generated based on the peripheral information acquired by the peripheral information acquisition device at the current position, and determine a position associated with the extracted two-dimensional image, as the position corresponding to the current position of the peripheral information acquisition device.

5. An image display method comprising:

moving, by a motor connected with a peripheral information acquisition device located inside a tubular member, the peripheral information acquisition device along an extending direction of the tubular member, the peripheral information acquisition device being configured to emit an ultrasound wave or light toward a periphery of the tubular member inside an organ or a blood vessel and acquire a reflected ultrasound wave or reflected light as peripheral information;

sequentially generating, by a processor, two-dimensional images based on the peripheral information acquired by the peripheral information acquisition device;

generating, by the processor, a three-dimensional image of the organ or the blood vessel based on the two-dimensional images sequentially generated;

storing, in a memory, position correspondence information indicating respective positions along a predetermined coordinate axis inside the three-dimensional image that correspond to positions of the motor or image correspondence information associating the respective positions along the predetermined coordinate axis inside the three-dimensional image with the two-dimensional images sequentially generated;

determining, by the processor, a position, from among the respective positions along the predetermined coordinate axis inside the three-dimensional image, corresponding to a current position of the peripheral information acquisition device based on the position correspondence information or the image correspondence information stored in the memory;

generating, in real time by the processor, display information including a first display area in which a two-dimensional image generated based on the peripheral information acquired by the peripheral information acquisition device at the current position is displayed, and a second display area in which the determined position corresponding to the current position of the peripheral information acquisition device is identified and displayed along with the three-dimensional image; and updating, by the processor, after the display information is previously displayed and the peripheral information acquisition device is moved, the display information such that a newly determined position corresponding to a position to which the peripheral information acquisition device has moved is identified and displayed in the second display area while a two-dimensional image generated based on the peripheral information acquired by the peripheral information acquisition device at the position to which the peripheral information acquisition device has moved is displayed in the first display area.

6. An image processing device comprising:

a memory; and a processor configured to:

sequentially generate two-dimensional images based on peripheral information acquired by a peripheral information acquisition device that is located inside a tubular member, is to be moved along an extending direction of the tubular member, and is configured to emit an ultrasound wave or light toward a periphery of the tubular member inside an organ or a blood vessel and acquire a reflected ultrasound wave or reflected light as the peripheral information, generate a three-dimensional image of the organ or the blood vessel based on the two-dimensional images sequentially generated;

store, in the memory, image correspondence information associating respective positions along a predetermined coordinate axis inside the three-dimensional image with the two-dimensional images sequentially generated;

determine a position, from among the respective positions along the predetermined coordinate axis inside the three-dimensional image, corresponding to a current position of the peripheral information acquisition device based on the image correspondence information stored in the memory;

generate, in real time display information including a first display area in which a two-dimensional image generated based on the peripheral information acquired by the peripheral information acquisition device at the current position is displayed, and a second display area in which the determined position corresponding to the current position of the peripheral information acquisition device is identified and displayed along with the three-dimensional image; and update, in a case where the display information is previously displayed and the peripheral information acquisition device has moved, the display information such that a newly determined position corresponding to a position to which the peripheral information acquisition device has moved is identified and displayed in the second display area while a two-dimensional image generated based on the peripheral information acquired by the peripheral information acquisition device at the position to which the peripheral information acquisition device has moved is displayed in the first display area.

* * * * *